United States Patent [19]

Sugama et al.

[11] Patent Number: 5,573,649
[45] Date of Patent: Nov. 12, 1996

[54] MINIATURIZED OXYGEN ELECTRODE AND PROCESS OF PRODUCING SAME

[75] Inventors: Akio Sugama; Hiroaki Suzuki; Naomi Kojima, all of Kawasaki, Japan

[73] Assignee: Fujitsu Limited, Kawasaki, Japan

[21] Appl. No.: 430,318

[22] Filed: Apr. 28, 1995

Related U.S. Application Data

[60] Continuation-in-part of Ser. No. 145,277, Nov. 3, 1993, which is a division of Ser. No. 850,834, Mar. 13, 1992, Pat. No. 5,281,323.

[30] Foreign Application Priority Data

Mar. 20, 1991 [JP] Japan ........................ 3-57220
May 28, 1991 [JP] Japan ........................ 3-123787

[51] Int. Cl.$^6$ .................................................. G01N 27/26
[52] U.S. Cl. .......................... 204/415; 204/403; 204/412; 205/778; 435/287.1; 435/287.5; 435/817; 435/287.9
[58] Field of Search ........................ 204/415, 403, 204/412, 153.12; 435/288, 291, 817

[56] References Cited

U.S. PATENT DOCUMENTS

| | | | |
|---|---|---|---|
| 4,001,042 | 1/1977 | Trocciola et al. ........................ | 427/115 |
| 4,496,451 | 1/1985 | Ishii et al. .............................. | 204/283 |
| 4,502,938 | 3/1985 | Covington et al. ..................... | 204/403 |
| 4,699,804 | 10/1987 | Miyata et al. ......................... | 427/255.6 |
| 4,874,500 | 10/1989 | Madou et al. ......................... | 204/412 |
| 4,975,175 | 12/1990 | Karube et al. ......................... | 204/412 |
| 5,133,856 | 7/1992 | Yamaguchi et al. .................... | 204/416 |
| 5,322,063 | 6/1994 | Allen et al. ............................ | 204/412 |

FOREIGN PATENT DOCUMENTS

| | | |
|---|---|---|
| 0030503 | 6/1981 | European Pat. Off. . |
| 0100667 | 2/1984 | European Pat. Off. . |
| 0284518 | 9/1988 | European Pat. Off. . |
| 2-236154 | 9/1990 | Japan . |
| 2-240556 | 9/1990 | Japan . |
| 4-125462 | 4/1992 | Japan . |
| 5-087766 | 4/1993 | Japan . |
| 6-001254 | 1/1994 | Japan . |

OTHER PUBLICATIONS

*Inspec Database* Abstract No. A86097437, Institute of Electrical Engineers, London, GB; S. J. Pace et al.: "A thick–film multi–layered oxygen sensor" & Transducers '85—1985 International Conference on Solid State Sensors & Actuators Digest of Technical Papers (Cat. No. 85CH2127-9) 1985, IEEE, New York, NY, pp. 406–409.
*Patent Abstracts of Japan*, vol. 11, No. 223 (P–597), Jul. 21, 1987 & JP–A–62–039755, Feb. 20, 1987.
*Patent Abstracts of Japan*, vol. 14, No. 554 (P–1140), Mar. 9, 1989 & JP–A–2–236154, Aug. 19, 1990.
*World Patents Index Latest* Derwent Publications Ltd., London, GB; Database WPIL Accession No. 90–330569, week 9044 & JP–A–2–236154, Aug. 19, 1990.

*Primary Examiner*—Bruce F. Bell
*Attorney, Agent, or Firm*—Staas & Halsey

[57] ABSTRACT

The miniaturized oxygen electrode having a small size exceeding the limit of miniaturization of the prior art electrode comprises an insulating substrate 21, 31 and, provided thereon, a pair of electrode patterns 22, 23 each comprising an active section 22A, 23A, a terminal section 22C, 23C for external connection, and a lead wire portion 22B, 23B for the connection thereof, the active sections 22A, 23A being mutually connected through an electrolyte-containing material 24, the electrolyte-containing material 24 being covered with an oxygen-permeable membrane 28, the lead wire portion 22B of at least one 22 of the electrode patterns extending below the active section 23A of at least one of other electrode patterns, 23, with an insulating layer 29 intervening between the lead wire portion 22B and the active section 23A.

29 Claims, 18 Drawing Sheets

(1)

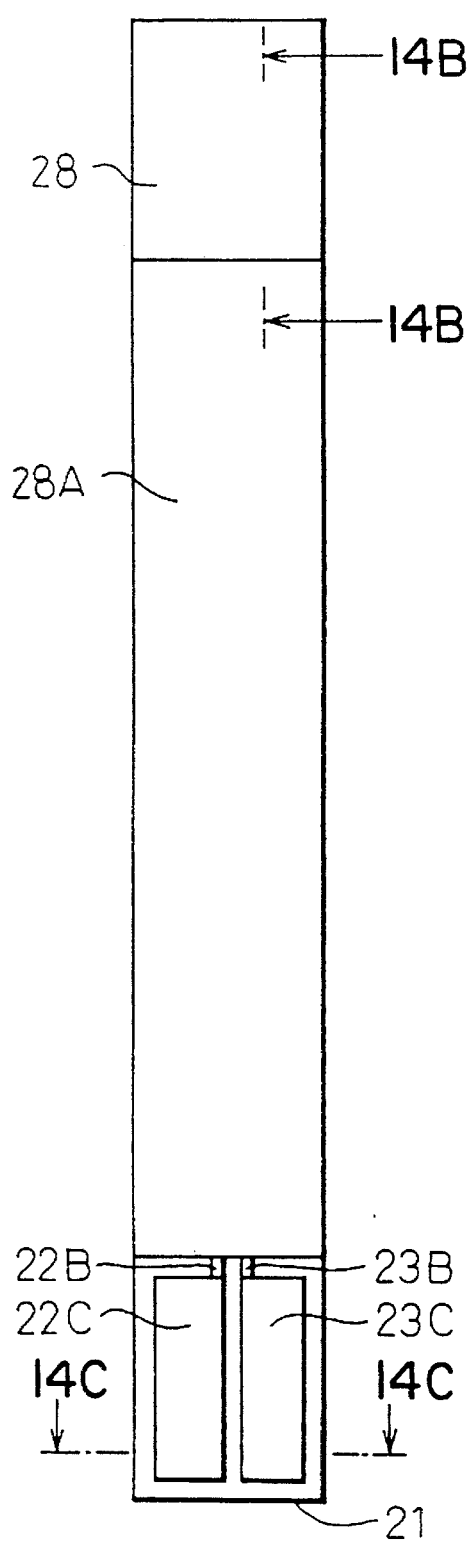
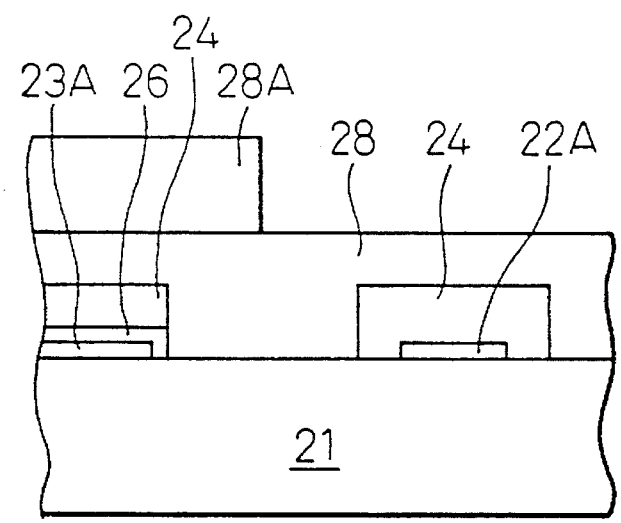
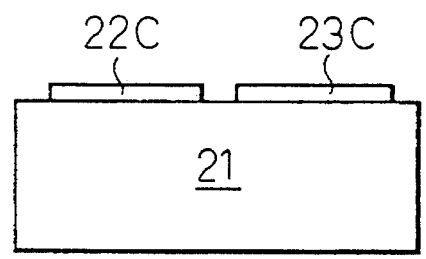
Fig.14A
Fig.14B
Fig.14C

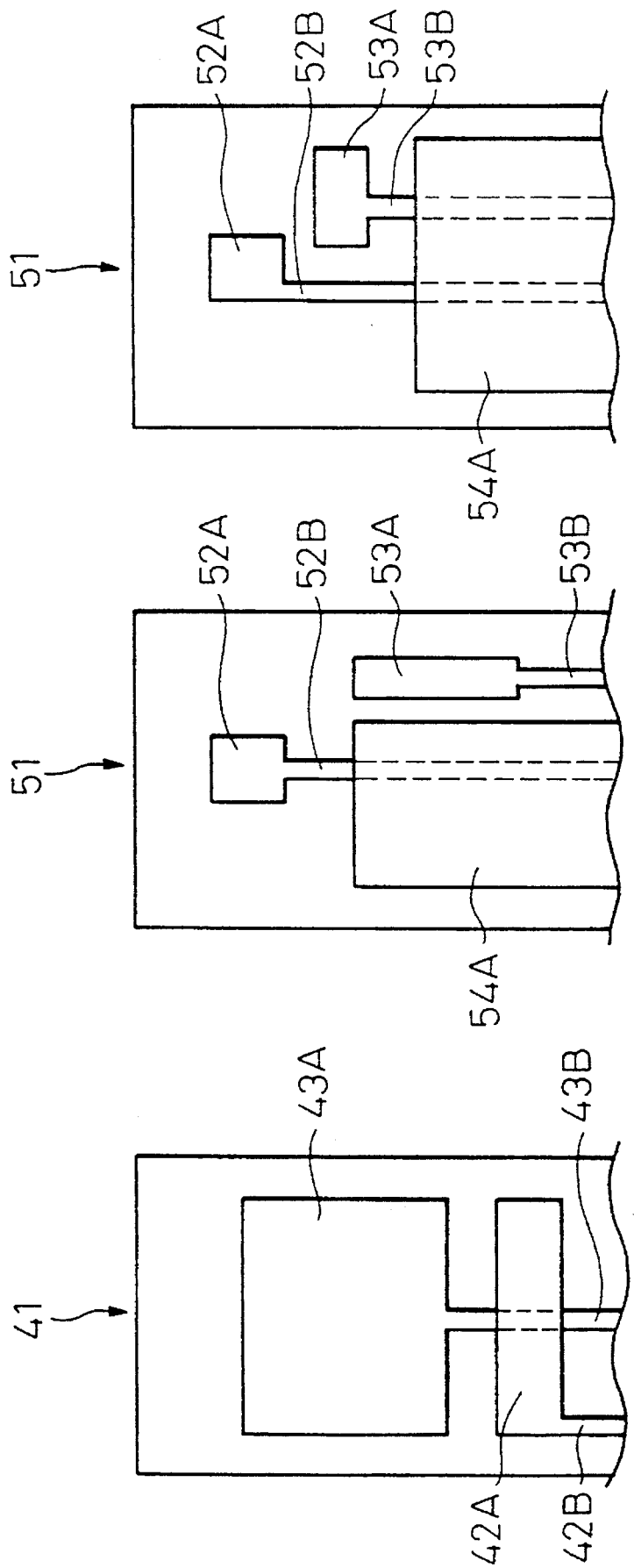

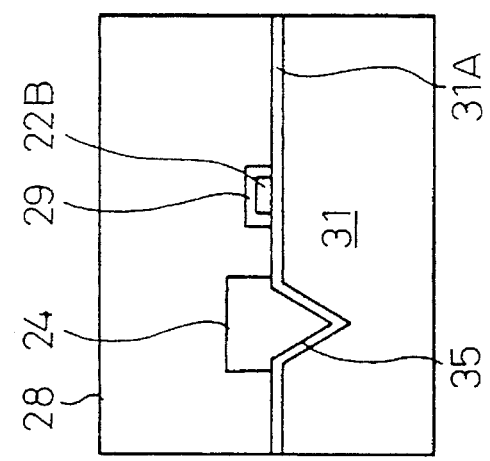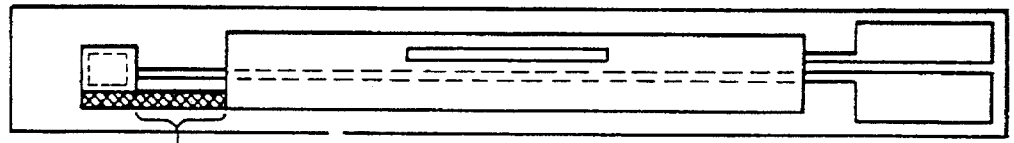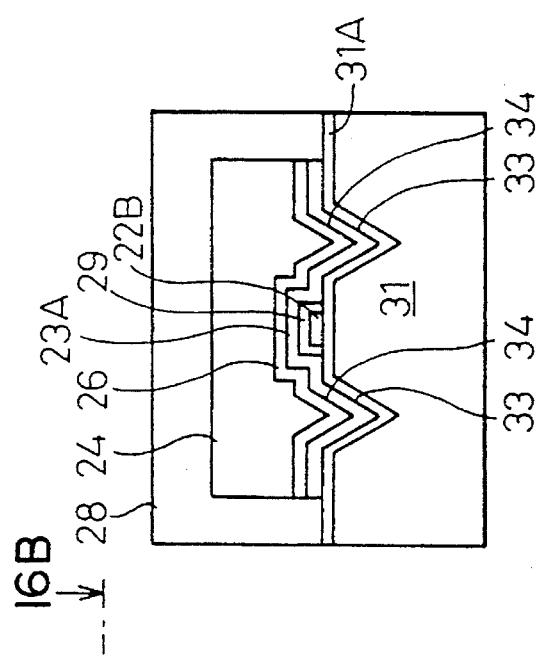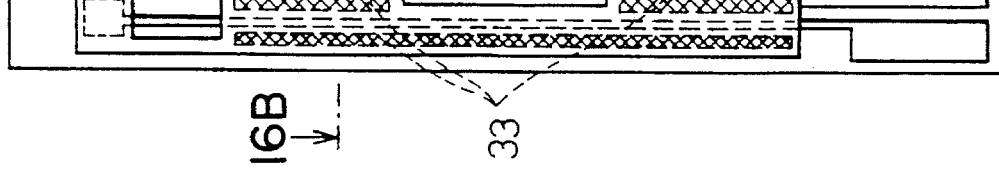

5,573,649

MINIATURIZED OXYGEN ELECTRODE AND PROCESS OF PRODUCING SAME

CROSS-REFERENCES TO RELATED APPLICATIONS

This application is a continuation-in-part application of U.S. Ser. No. 08/145,277 filed on Nov. 3, 1993, which is a divisional application of U.S. Ser. No. 07/850,834 filed on Mar. 13, 1992 and issuing as U.S. Pat. No. 5,281,323 on Jan. 25, 1994.

BACKGROUND OF THE INVENTION

1. Field of the Invention

The present invention relates to an improvement in the structure of a miniaturized oxygen electrode which can be mass-produced at a low cost.

A miniaturized oxygen electrode can be advantageously used for the measurement of oxygen concentration in various fields. For example, the miniaturized oxygen electrode is used for the measurement of biological oxygen demand (BOD) in water from the viewpoint of water control. In the fermentation industry, the regulation of the dissolved oxygen concentration in the fermentation tank is necessary for fermentation with a high efficiency. A miniaturized oxygen electrode is used as a measuring instrument for this purpose. Further, a miniaturized oxygen electrode can be combined with an enzyme to form a biosensor which can be used for the measurement of the concentration of sugar or alcohols. For example, glucose is reacted with dissolved oxygen in the presence of a catalyst of glucose oxidase, an enzyme, causing the glucose to be oxidized to gluconolactone. This reduces the amount of dissolved oxygen diffusing into an oxygen electrode. By taking advantage of this phenomenon, the glucose concentration can be measured based on the consumption of dissolved oxygen.

Thus, the miniaturized oxygen electrode is utilized in various fields, including environmental instrumentation, the fermentation industry, and clinical care. In particular, in medical care, the miniaturized oxygen electrode as the glucose sensor for patients suffering from diabetes is of high utility value because it is small, disposable and low cost.

2. Description of the Related Art

Glass or vinyl chloride oxygen electrodes of Clark type have been used as the oxygen electrode. However, the electrodes could neither be miniaturized nor mass-produced.

For this reason, the present inventors have proposed a new type of miniaturized oxygen electrode that can be produced through the utilization of lithography and anisotropic etching (see Japanese Unexamined Patent Publication (Kokai) No. 63-238548: Japanese Examined Patent Publication (Kokoku) No. 6-1254). This miniaturized oxygen electrode comprises a structure produced by forming a hole on a silicon substrate by anisotropic etching, forming two electrodes through an insulating layer on the bottom of the hole, filling the hole with an electrolyte-containing material and finally covering the upper surface of the hole with a gas-permeable membrane. Further, the present inventors have developed a technique where an electrolyte-containing material and a gas-permeable membrane are provided only in a requisite place by taking advantage of screen printing (Japanese Unexamined Patent Publication (Kokai) No. 5-87766). This miniaturized oxygen electrode has a small size, gives rise to no scattering of properties and can be collectively mass-produced, which renders the production cost low.

FIGS. 1A and 1B are respectively a plan view of the conventional miniaturized oxygen electrode of the type described above and a cross-sectional view taken on line 1B—1B of FIG. A1 In the drawing, numeral 1 designates a miniaturized oxygen electrode. The miniaturized oxygen electrode 1 comprises a rectangular silicon substrate 11 having on its whole surface an insulating layer of $SiO_2$ comprising a pair of a cathode pattern 12 and an anode pattern 13 each as a silver layer, the cathode pattern 12 and the anode pattern 13 comprising an active section 12A, 13A, a terminal 12C, 13C for external connection, and a lead wire 12B, 13B for the connection thereof. The active portions 12A, 13A are connected to each other through an electrolyte-containing material 14. The active portion 12A of the cathode pattern 12 serves substantially as a cathode, while the active portion 13A of the anode pattern 13 serves substantially as an anode.

In the region where the cathode 12A overlaps the electrolyte-containing material 14, these elements are in contact with each other through an opening 15 provided in a hydrophobic layer (not shown), interposed between the elements, such as a photoresist, and an oxygen-sensitive section (a measuring section) 12S is defined by the opening 15.

In the region where the anode 13A overlaps with the electrolyte-containing material 14, these elements are in contact with each other through an opening 17 provided in a water-impermeable membrane 16, such as a polyimide, interposed between both the elements.

The electrolyte-containing material 14 is covered with an oxygen-permeable membrane 18 (FIG. 1B). The oxygen-permeable membrane 18 covers the whole substrate region except for the substrate region at the portion which includes terminals (pads) 12C, 13C (i.e., in FIG. 1A, the whole region above the terminals 12C, 13C is covered.)

When the miniaturized oxygen electrode shown in FIGS. 1A and 1B is used, a certain voltage, which is negative with respect to the anode, is applied to the cathode. The immersion of the sensitive section in this state in a buffer causes dissolved oxygen to pass through the oxygen- or gas-permeable membrane and reach the working electrode (cathode), where the dissolved oxygen is reduced. A current generated by the reduction reaction can be measured to determine the dissolved oxygen concentration using the current value as a measure.

Further, in order to render the miniaturized oxygen electrode more suitable for actual production in a plant and, at the same time, to further improve the performance, the present inventors have developed, as a miniaturized oxygen electrode of the above type, a miniaturized oxygen electrode using a combination of anisotropic etching with anodic bonding (Japanese Unexamined Patent Publication (Kokai) No. 4-125462).

In all the above miniaturized oxygen electrode production techniques, lithography is carried out using as materials a silicon substrate and a glass substrate. Therefore, even though optimal conditions in respect of equipment and the like are prepared and the demand is about several ten million chips per year, it is impossible to reduce the cost to a low value compatible to that of test paper, and not more than 100 yen per chip. For this reason, in order to further reduce the cost, the present inventors have developed a miniaturized oxygen electrode wherein a plastic substrate was used, an electrolyte was impregnated into paper and a gas-permeable membrane was adhered to a sensitive section (Japanese Unexamined Patent Publication (Kokai) No. 6-34596).

The above conventional miniaturized oxygen electrode is much smaller than the old Clark oxygen electrode. In recent years, however, in the field of medical care, for example, there is an increasing demand for the insertion of an oxygen electrode into a blood vessel of a patient to directly measure various components present in the blood. In such applications, the size of the miniaturized oxygen electrode should be reduced to, for example, not more than 1 mm in width. In the case of the conventional miniaturized oxygen electrode shown in FIGS. 1A and 1B, the size could not be reduced to less than about 2 mm in width.

SUMMARY OF THE INVENTION

An object of the present invention is to provide a miniaturized oxygen electrode having a smaller size than the conventional miniaturized oxygen electrode, exceeding the limit of miniaturization of the prior art electrode.

In order to attain the above object, according to the present invention, there is provided a miniaturized oxygen electrode comprising an insulating substrate and, provided thereon, a set of electrode patterns each comprising an active section, a terminal section for external connection, and a lead wire portion for the connection thereof, the active sections being mutually connected through an electrolyte-containing material, said electrolyte-containing material being covered with an oxygen-permeable membrane, the lead wire portion of at least one of the electrode patterns extending below the active section of the other at least one of other electrode patterns, with an insulating layer intervening between the lead wire portion and the active section.

For the conventional miniaturized oxygen electrode, a cathode and an anode 12A, 13A, lead wire portions 12B, 13B for the connection thereof, and pads 12C, 13C are disposed parallel to one another on the same plane, as shown in FIGS. 1A and 1B. In many cases, this structure poses no problem. However, in an attempt to further miniaturize the oxygen electrode, even the space occupied by the lead wires becomes important. In the miniaturized oxygen electrode, unlike in semiconductor ICs, the gap between the lead wire and the other electrode pattern cannot be reduced to, for example, about 1 μm.

The reason for this is as follows. When the miniaturized oxygen electrode is used, water is introduced thereinto. Therefore, if the cathode and the anode in their portions in contact with an electrolyte are not at a sufficient distance from the lead wire portion, for example, peeling of the oxygen- or gas-permeable membrane causes the electrolyte to permeate and reach the lead wire portion, causing a reaction. For this reason, in order to ensure the reliability of the miniaturized oxygen electrode, the patterns including the lead wire portion should be separated from each other by 100 to 200 μm or more. This makes it impossible to reduce the size of the conventional miniaturized oxygen electrode to not more than 1 mm in width.

In the miniaturized oxygen electrode of the present invention, the lead wire portion of at least one of the electrode patterns extends below the active section of at least one of other electrodes, with an insulating layer intervening between the lead wire portion and the active section. This three-dimensional arrangement, as compared with the conventional planar arrangement, enables a larger number of patterns to coexist in an identical substrate area and, consequently, the width of the miniaturized oxygen electrode to be further reduced as compared with the conventional oxygen electrode. In this case, the insulation of the patterns laminated in a three-dimensional manner from each other is ensured by an insulating layer interposed between the patterns, and, even though peeling of the oxygen- or gas-permeable membrane occurs, there is no possibility that the electrolyte reaches the lead wire portion.

BRIEF DESCRIPTION OF THE DRAWINGS

FIGS. 1A and 1B show a conventional miniaturized oxygen electrode, wherein FIG. 1A is a plan view and FIG. 1B is a cross-sectional view thereof in its central portion;

FIGS. 2A, 2B and 2C show a miniaturized oxygen electrode of the present invention, wherein FIG. 2A is a plan view thereof, FIG. 2B is a cross-sectional view thereof at its central portion and FIG. 2C is a cross-sectional view of another embodiment thereof at its central portion;

FIGS. 3A, 3B and 3C show the first step of preparing the miniaturized oxygen electrode of the present invention shown in FIGS. 2A and 2B, wherein FIG. 3A is a plan view of a miniaturized oxygen electrode in this stage, FIG. 3B is a cross-sectional view thereof in its central portion and FIG. 3C is a partially enlarged cross-sectional view thereof;

FIGS. 4A and 4B show the step following the step shown in FIGS. 3A, 3B and 3C, wherein FIG. 4A is a plan view of a miniaturized oxygen electrode in this stage and FIG. 4B is a cross-sectional view thereof in its central portion;

FIGS. 5A, 5B and 5C show the step following the step shown in FIGS. 4A and 4B, wherein FIG. 5A is a plan view of a miniaturized oxygen electrode in this stage, FIG. 5B is a cross-sectional view thereof in its central portion and FIG. 5C is a partially enlarged cross-sectional view thereof;

FIGS. 6A, 6B and 6C show the step following the step shown in FIGS. 5A, 5B and 5C, wherein FIG. 6A is a plan view of a miniaturized oxygen electrode in this stage, FIG. 6B is a cross-sectional view thereof in its central portion and FIG. 6C is a partially enlarged cross-sectional view thereof;

FIGS. 7A and 7B show the step following the step shown in FIGS. 6A, 6B and 6C, wherein FIG. 7A is a plan view of a miniaturized oxygen electrode in this stage and FIG. 7B is a cross-sectional view thereof in its central portion;

FIGS. 8A and 8B show the step following the step shown in FIGS. 7A and 7B, wherein FIG. 8A is a plan view of a miniaturized oxygen electrode in this stage and FIG. 8B is a cross-sectional view thereof in its central portion;

FIGS. 9A, 9B and 9C show the step following the step shown in FIGS. 8A and 8B, wherein FIG. 9A is a plan view of a miniaturized oxygen electrode in this stage, FIG. 9B is a longitudinal sectional view thereof in and around its sensitive section and FIG. 9C is a cross-sectional view thereof in its pad region;

FIGS. 10A, 10B, 10C and 10D show the step following the step shown in FIGS. 9A, 9B and 9C, wherein FIG. 10A is a plan view of a miniaturized oxygen electrode in this stage, FIG. 10B is a longitudinal sectional view thereof in and around its sensitive section, FIG. 10C is a cross-sectional view thereof in its central portion and FIG. 10C is a cross-sectional view thereof in its pad region;

FIGS. 11A, 11B and 11C show the step following the step shown in FIGS. 10A, 10B, 10C and 10D, wherein FIG. 11A is a plan view of a miniaturized oxygen electrode in this stage, FIG. 11B is a cross-sectional view thereof in its central portion and FIG. 11C is a cross-sectional view thereof in its pad region;

FIGS. 12A, 12B and 12C show a miniaturized oxygen electrode in such a state that a second peelable mask has been formed on an oxygen-permeable membrane in its portion around a sensitive section, wherein FIG. 12A is a plan view thereof, FIG. 12B is a longitudinal sectional view thereof in and around its sensitive portion and FIG. 12C is a cross-sectional view thereof in its pad region;

FIGS. 13A, 13B and 13C show a miniaturized oxygen electrode in such a state that, after the formation of a second peelable mask, a second oxygen-permeable membrane has been formed on the whole surface thereof, wherein FIG. 13A is a plan view thereof, FIG. 13B is a longitudinal sectional view thereof in and around its sensitive portion and FIG. 13C is a cross-sectional view thereof in its pad region;

FIGS. 14A, 14B and 14C show a miniaturized oxygen electrode of the present invention in such a state that the first and second peelable masks have been peeled off to form a thin oxygen-permeable membrane in the sensitive portion, wherein FIG. 14A is a plan view thereof, FIG. 14B is a longitudinal sectional view thereof in and around its sensitive section and FIG. 14C is a cross-sectional view thereof in its pad region;

FIGS. 15A, 15B and 15C show a miniaturized oxygen electrode of the present invention, wherein FIG. 15A is a plan view thereof having another embodiment of the bipolar construction, FIG. 15B is a plan view thereof having a tripolar construction and FIG. 15C is a plane view thereof having another embodiment of the tripolar construction;

FIGS. 16A, 16B, 16C and 16D shows an embodiment of the miniaturized oxygen electrode according to the present invention, having a groove (a recess) to be filled with an electrolyte-containing material, wherein 16A and 16C are plan views and 16B and 16D are cross-sectional views;

DESCRIPTION OF THE PREFERRED EMBODIMENTS

Example 1

Figure 2A:
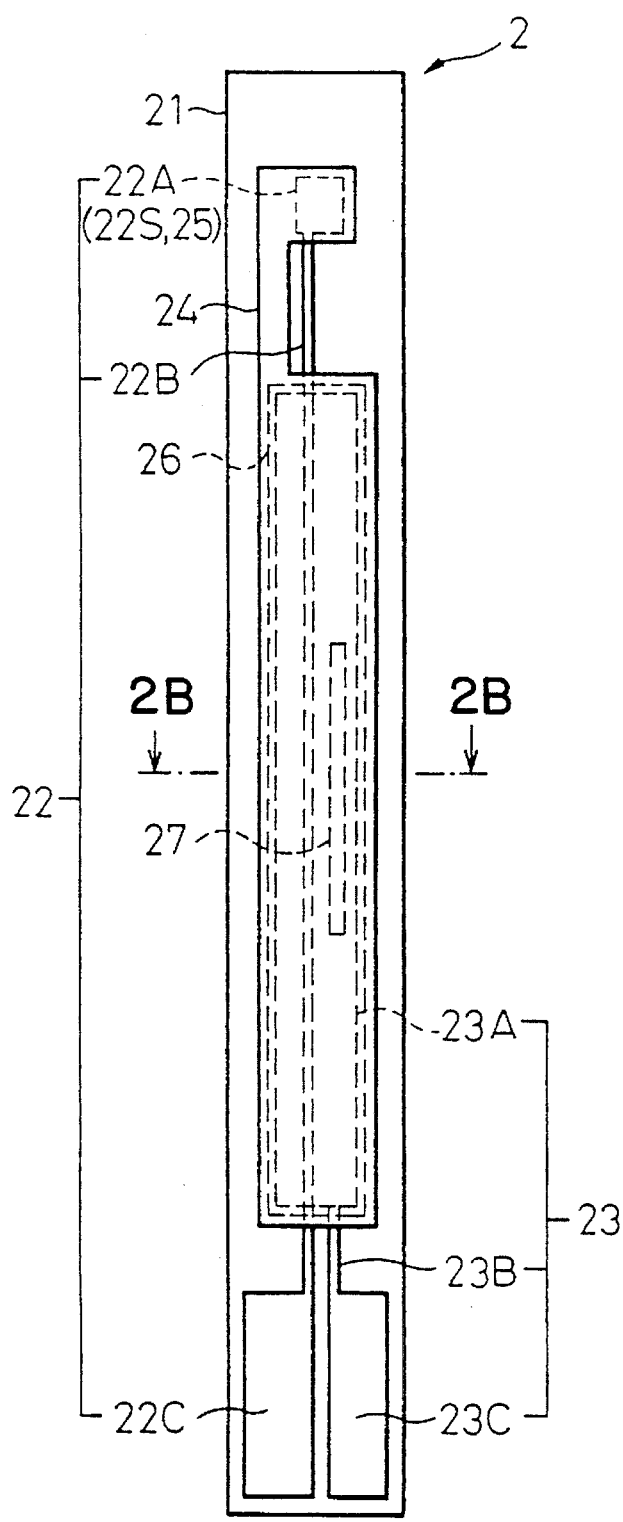
Figure 2B:
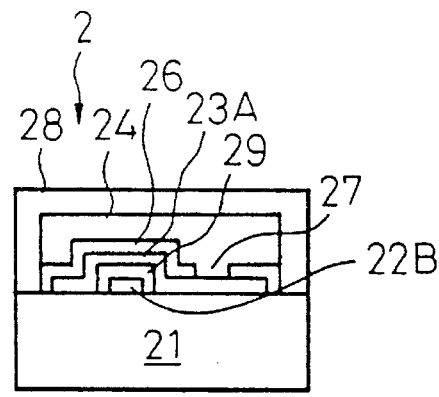
Figure 2C:
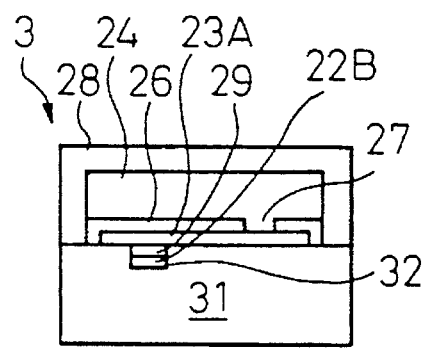
Figure 3A:
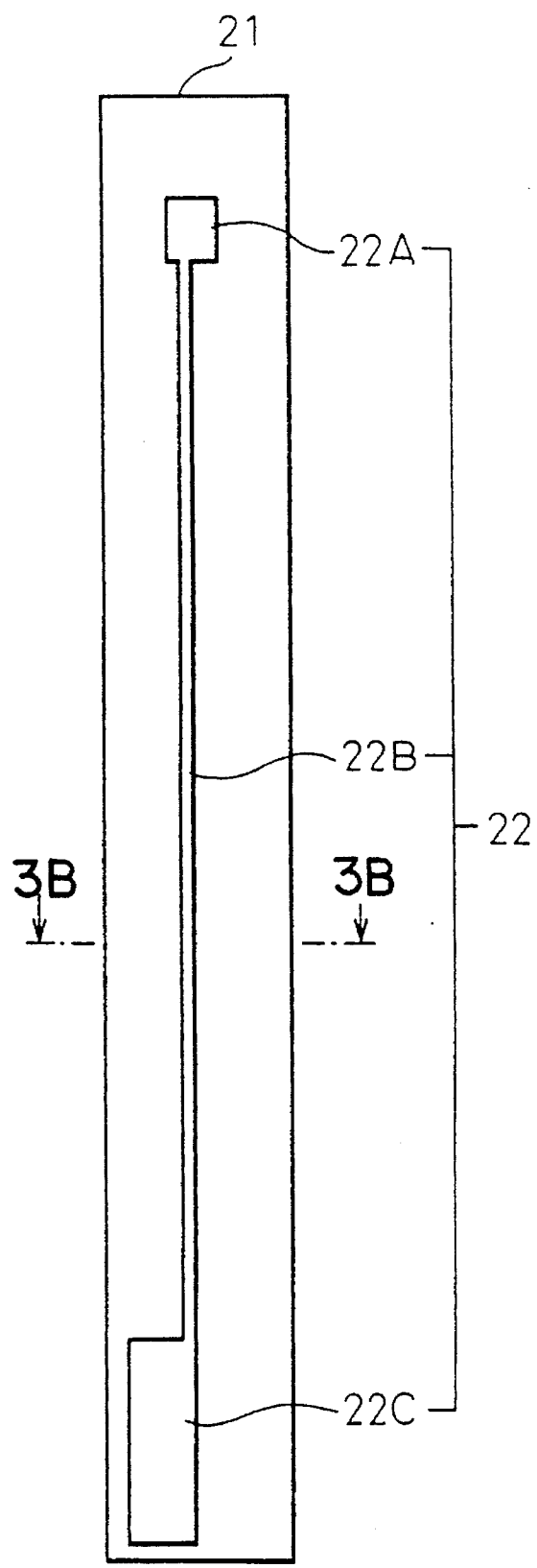
Figure 3B:
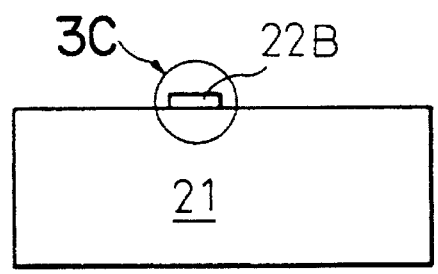
Figure 3C:
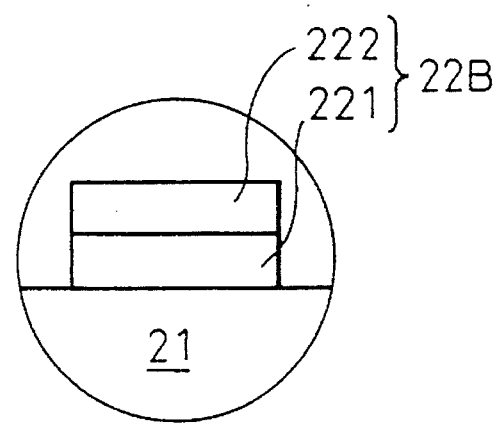

FIGS. 2A, 2B and 2C show a miniaturized oxygen electrode of the present invention, wherein FIG. 2A is a plan view thereof and FIG. 2B is a cross-sectional view taken on line 2B—2B of FIG. 2A.

Figure 1A:
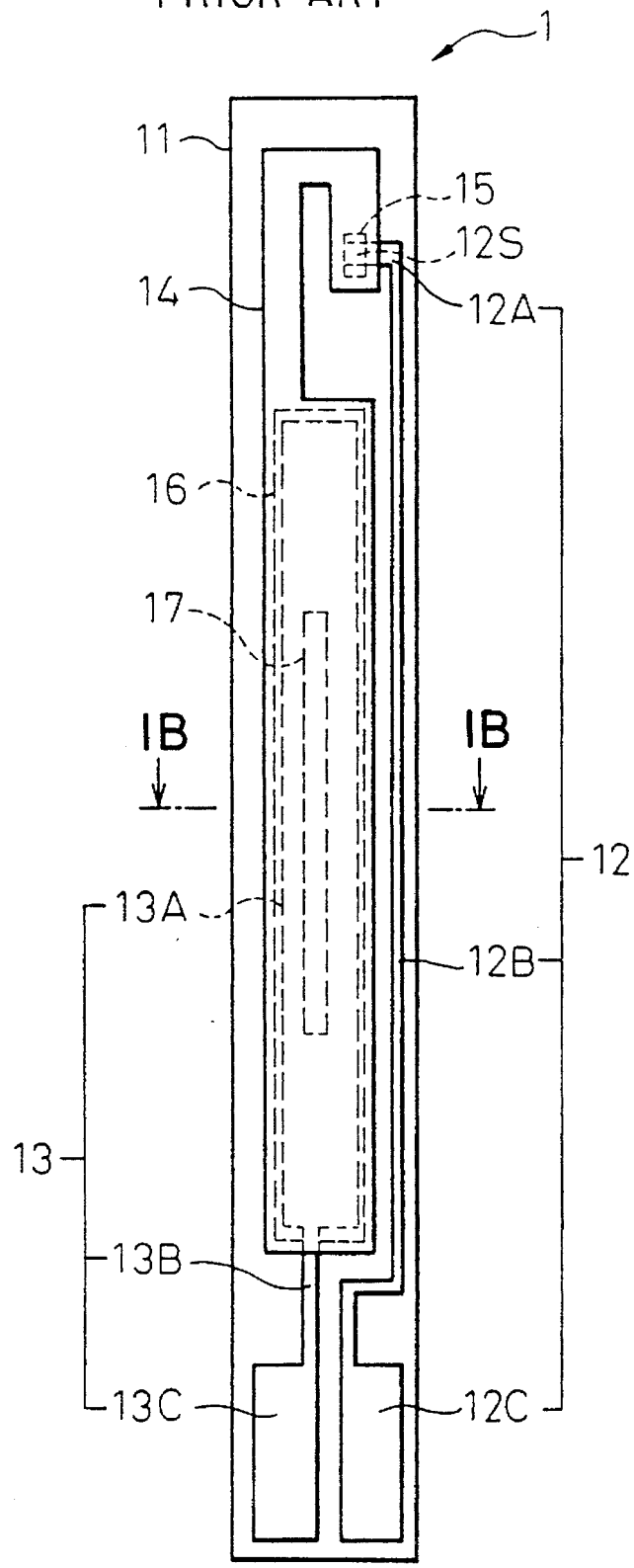
Figure 1B:
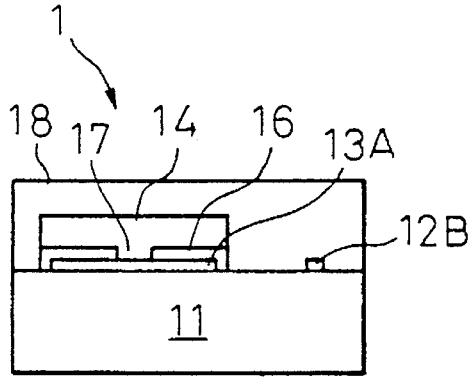

In a miniaturized oxygen electrode 2 according to the present invention, a lead wire portion 22B of a cathode pattern 22 extends below an active section (substantial anode) 23A of an anode pattern 23, with an insulating layer 29 intervening between the lead wire portion 22B and the active section 23A. The three-dimensional arrangement of the lead wire portion 22B for the cathode relative to the anode 23A enables the width of the miniaturized oxygen electrode to be reduced as compared with the conventional planar arrangement shown in FIGS. 1A and 1B.

The miniaturized oxygen electrode 2 of the present invention comprises a glass substrate 21 and, provided thereon, a pair of a cathode pattern 22 and an anode pattern 23 each comprising an active section 22A, 23A, a terminal section 22C, 23C for external connection, and a lead wire portion 22B, 23B for the connection thereof, said cathode pattern 22 and said anode pattern 23 each having a two-layer structure of a chromium layer as a lower layer and a gold layer as an upper layer. Each of the active sections 22A, 23A further comprises a silver layer on the gold layer of the above two-layer structure. The active sections 22A and 23A are mutually connected through an electrolyte-containing material 24 in direct contact with the silver layers. The active section 22A of the cathode pattern 22 substantially constitutes a cathode, while the active section 23A of the anode pattern 23 substantially constitute an anode.

In the region where the cathode 22A is overlapped with the electrolyte-containing material 24, these elements are in contact with each other through an opening 25 provided in a hydrophobic layer (not shown), interposed between both the elements, such as a photoresist, and an oxygen-sensitive section (a measuring section) 22S is defined by the opening 25.

In the region where the anode 23A is overlapped with the electrolyte-containing material 24, these elements are in contact with each other through an opening 27 provided in a water-impermeable membrane 26, interposed between both the elements, such as a polyimide. The water-impermeable membrane 26, such as a polyimide, covers also the lead wire portion 23B of the anode pattern 23.

The electrolyte-containing material 24 is covered with an oxygen-permeable membrane 28 (FIG. 2B) which has been formed on the whole surface of the substrate in the final stage. The oxygen-permeable membrane 28 covers the whole substrate region except for the substrate region in its portion including terminals (pads) 22C, 23C (i.e., in FIG. 2A, the whole region above the terminals 22C, 23C being covered.)

A process sequence for preparing a miniaturized oxygen electrode of the present invention as shown in FIGS. 2A, 2B and 2C will now be described with reference to FIGS. 3 to 11. In the present example, although the sequence is described for a single miniaturized oxygen electrode chip, for simplicity, a number of miniaturized oxygen electrodes are simultaneously formed on a single substrate in an actual production process.

Step 1: Formation of electrode pattern and insulating layer

A cathode pattern 22, an anode pattern 23, and an insulating layer 29 were formed according to the following procedure.

1-1: Formation of cathode pattern 22 (FIGS. 3(1): 3(2) and 3(3))

[1] A 500 μm-thick glass substrate 21 was prepared and cleaned with a solution mixture of hydrogen peroxide and ammonia and with concentrated nitric acid.

[2] A chromium layer 221 (thickness 400 Å) and a gold layer 222 (thickness 1500 Å) were formed in that order by vacuum deposition on one surface of the as-cleaned glass substrate 21.

[3] A positive-working photoresist (OFPR-5000, manufactured by Tokyo Ohka Kogyo Co., Ltd.) was spin-coated on the surface of the above substrate and then prebaked at 80° C. for 30 min. The prebaked coating was exposed and developed to form a photoresist pattern for etching.

[4] The gold layer 222 and the chromium layer 221 were successively etched with an etchant having the following composition, and the photoresist pattern was removed with acetone to form a cathode pattern 22 comprising an active section (cathode) 22A, a lead wire portion 22B, and a terminal section (pad) 22C for external connection.

Etchant for gold: $I_2$ (1 g)+KI (4 g)+water (4 ml)

Etchant for chromium: NaOH (0.5 g)+$K_3Fe(CN)_6$ (1 g)+water (4 ml)

[5] The substrate was cleaned with a solution mixture of hot hydrogen peroxide and ammonia and with pure water and then dried.

Figure 4A:
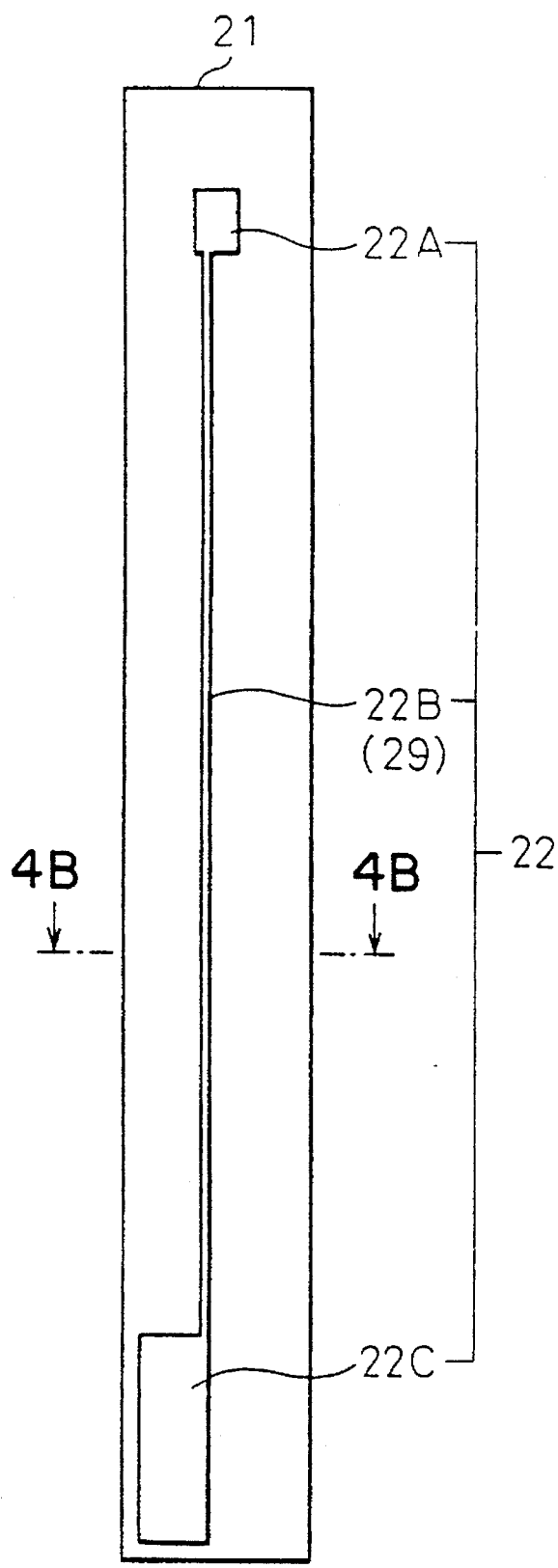
Figure 4B:
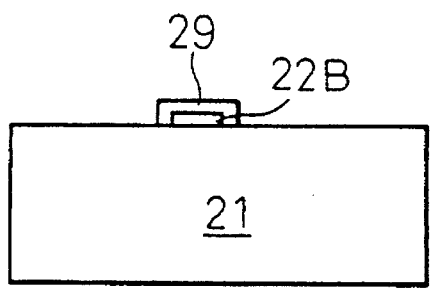

1-2: Formation of insulating layer covering lead wire portion (FIGS. 4A and 4B)

[6] A photosensitive polyimide stock (precursor) solution (Photoneece UR-3140, manufactured by Toray Industries, Inc.) was coated on the surface of the substrate having a cathode pattern 22 formed in the above [4] (spin coating conditions: 2300 rpm, 30 sec), and the coating was prebaked at 80° C. for 90 min.

[7] Ultraviolet light was applied only to the polyimide coating of the lead wire portion 22B.

[8] The polyimide coating was developed in a developing solution (DV-605, manufactured by Toray Industries, Inc.) and then rinsed, three times, in isopropyl alcohol.

[9] The developed polyimide coating was baked at 150° C. for 30 min, 200° C. for 30 min, and 300° C. for 1 hr in that order to cure the polyimide, thus forming a polyimide insulating layer 29 covering the lead wire portion 22B of the cathode pattern 22.

Figure 5A:
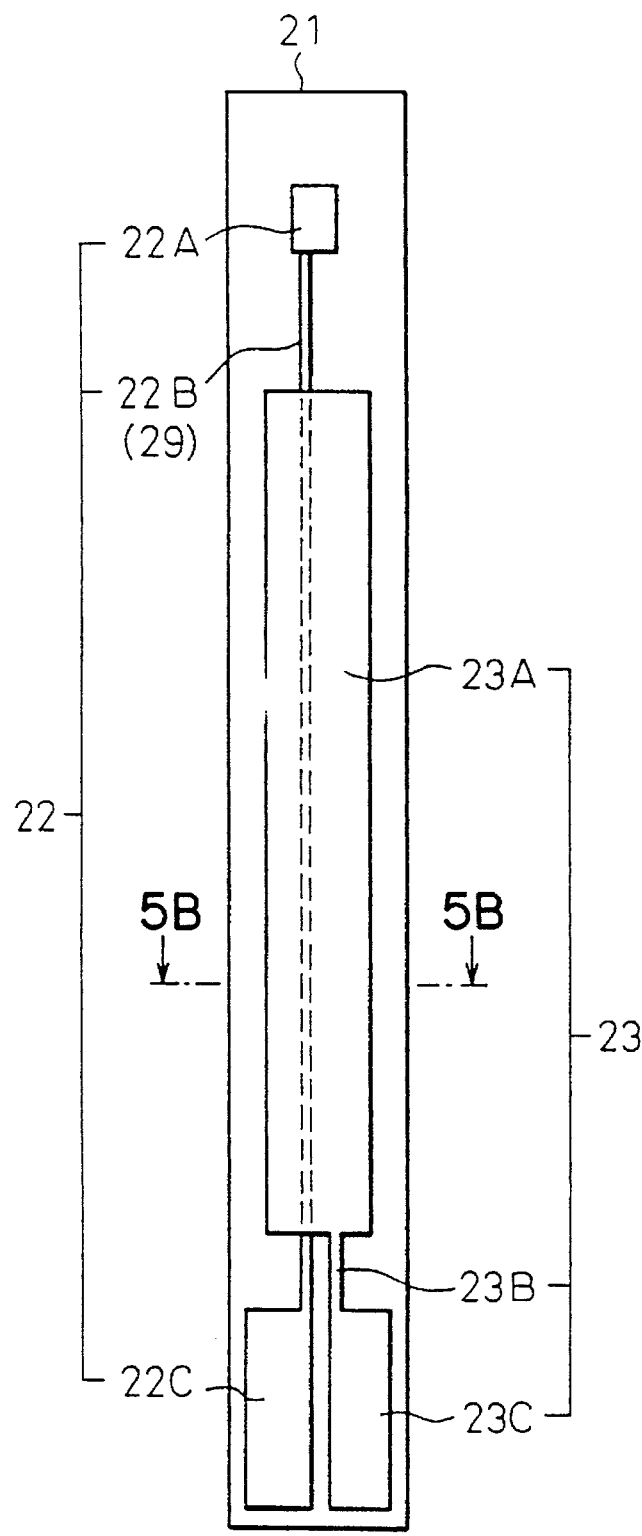
Figure 5B:
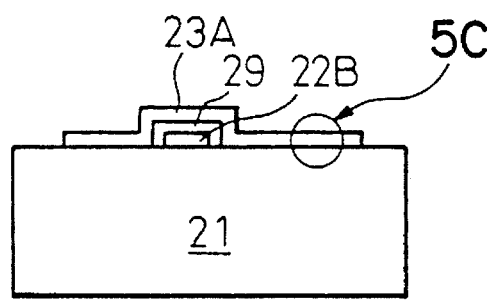
Figure 5C:
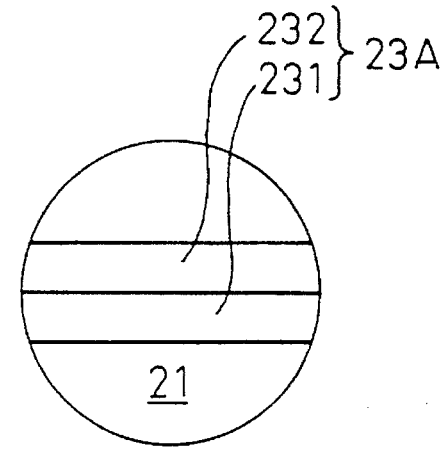

1-3: Formation of anode pattern (FIGS. 5A, 5B and 5C)

[10] A chromium layer 231 (thickness 400 Å) and a gold layer 232 (1000 Å) were formed in that order by vacuum deposition on the same surface of the substrate.

[11] A positive-working photoresist (OFPR-5000, manufactured by Tokyo Ohka Kogyo Co., Ltd.) was spin-coated on the same surface of the substrate and then prebaked at 80° C. for 30 min. The prebaked coating was exposed and developed to form a photoresist pattern for etching.

[12] The gold layer 232 and the chromium layer 231 were successively etched with an etchant having the same composition as used in the above [4], and the photoresist pattern was removed with acetone to form an anode pattern 23 comprising an active section (anode) 23A, a lead wire portion 23B, and a terminal section (pad) 23C for external connection.

Figure 6A:
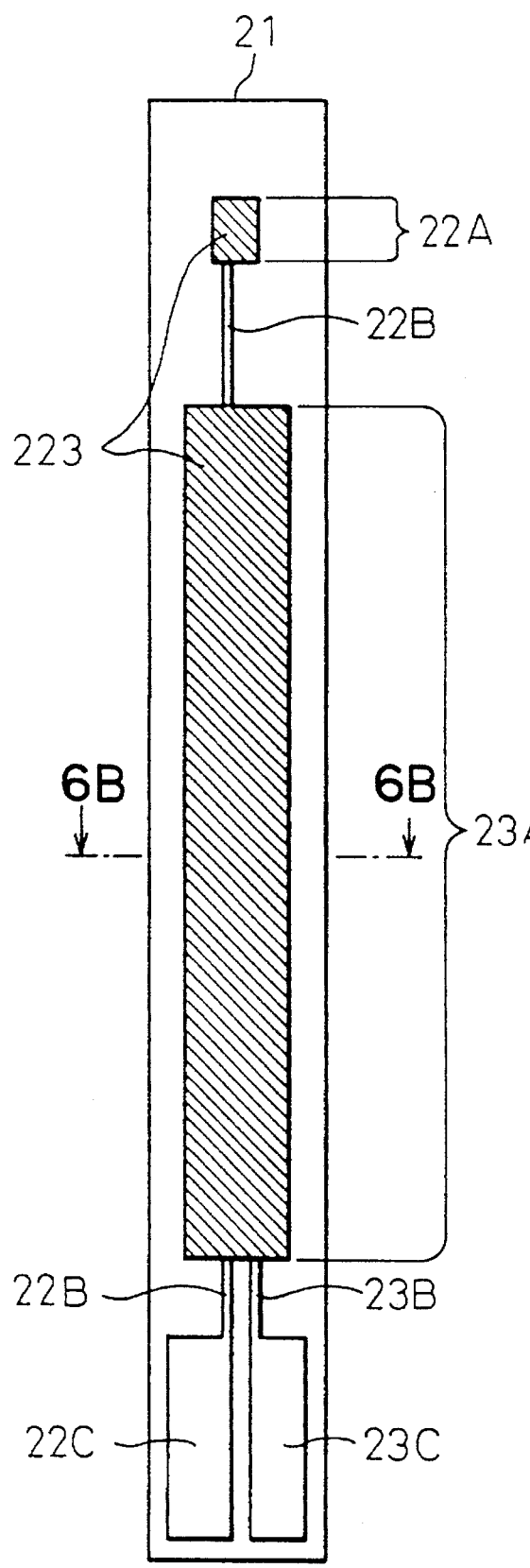
Figure 6B:
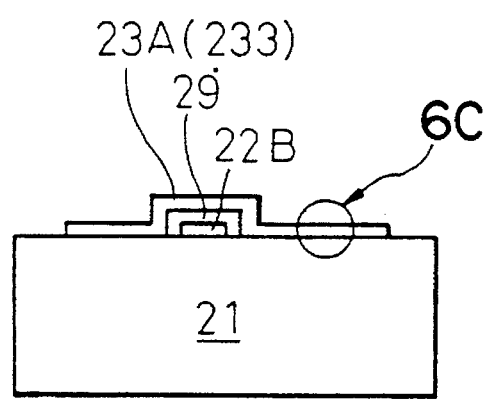
Figure 6C:
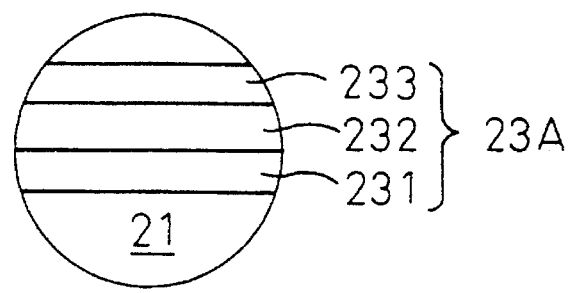

Step 2: Definition of active section (cathode and anode) (FIGS. 6A, 6B and 6C)

[13] A positive-working photoresist (OFPR-800, manufactured by Tokyo Ohka Kogyo Co., Ltd.) was coated on the whole surface of the same substrate, and the resultant coating was prebaked at 80° C. for 30 min, exposed, and then developed by immersing in toluene at 30° C. for 5 min, post-baked at 80° C. for 10 min. Thus, a photoresist pattern was formed which covered the whole substrate region except for the active sections of the electrode pattern, i.e., the cathode 22A and the anode 23A.

[14] A silver layer was formed by vacuum deposition on the whole surface of the same substrate, and the resist was then removed with acetone. The whole silver layer except for the active sections 22A, 23A were removed by a lift off process. Thus, active sections wherein the outermost layer comprised a silver layer 233 (FIG. 6C), that is, cathode 22A and anode 23A (FIG. 6A), were defined.

Figure 7A:
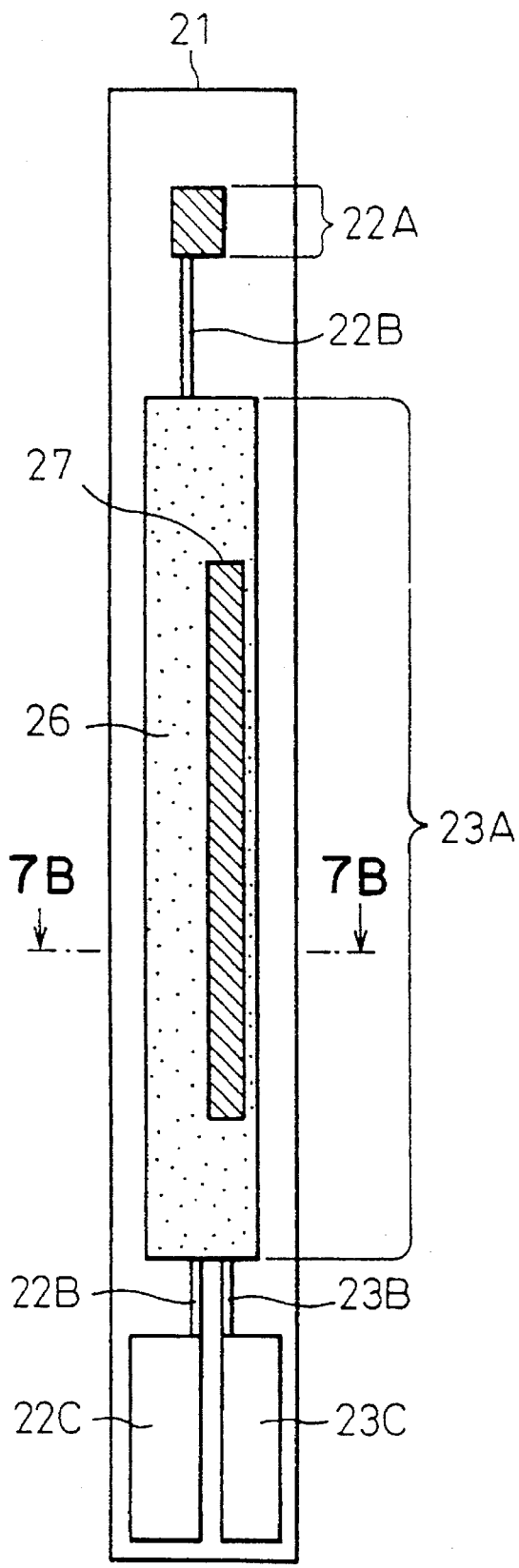
Figure 7B:
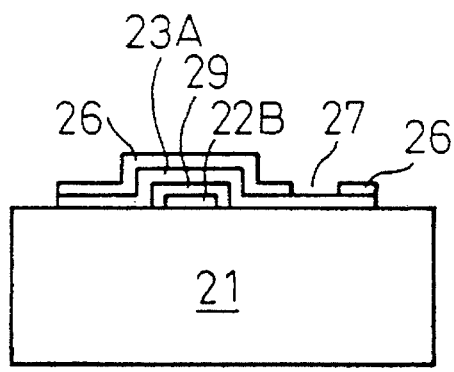

Step 3: Formation of water-impermeable membrane (FIGS. 7A and 7B)

[15] A photosensitive polyimide stock solution (Photoneece UR-3140, manufactured by Toray Industries, Inc.) was coated on the whole surface of the same substrate (spin coating conditions: 2300 rpm, 30 sec), and the resultant coating was prebaked at 80° C. for 90 min. As in the case of the above [7], ultraviolet light was applied only to the polyimide coating of the lead wire portion 23B of the anode pattern 23 and the polyimide coating of the active section (anode) 23A except for a portion where an opening 27 was formed. As in the case of the above [8], a polyimide coating was developed with a developing solution (DV-605, manufactured by Toray Industries, Inc.) and then rinsed in isopropyl alcohol three times.

[16] The developed polyimide coating was baked at 150° C. for 30 min, 200° C. for 30 min, and 250° C. for 15 min in that order to cure the polyimide, thus forming an electrolyte-impermeable or water-impermeable polyimide layer 26 covering the lead wire portion 23B and the most part of the anode 23A except for the opening 27.

Figure 8A:
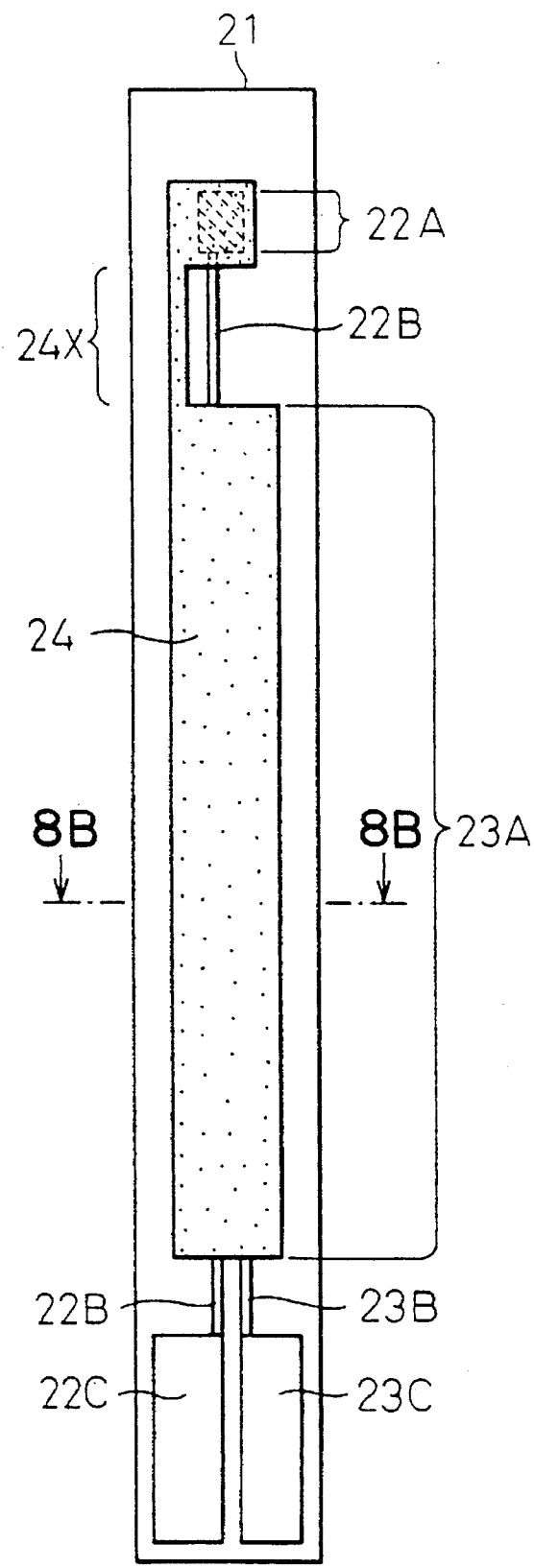
Figure 8B:
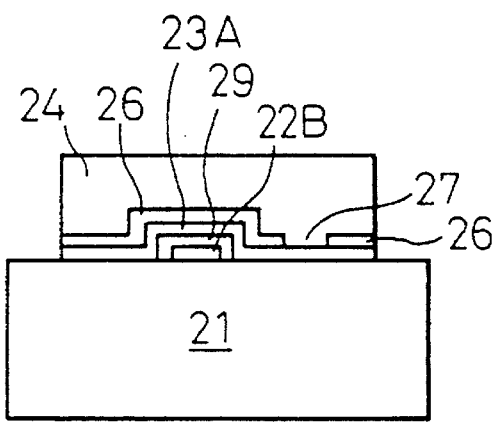

Step 4: Formation of electrolyte-containing material (FIGS. 8A and 8B)

[17] An electrolyte-containing material 24 was screen-printed on the cathode 22A, the anode 23A, and a liquid junction 24X for electrically connecting the cathode 22A and the anode 23A. The electrolyte-containing material 24 used was prepared by dispersing powdered potassium chloride, trishydroxymethylaminomethane, and glycine in a solution of polyvinyl pyrrolidone in alcohol. After screen printing, the solvent was removed by evaporation.

Step 5: Formation of oxygen-permeable membrane (FIGS. 9A, 9B, 9C, 10A, 10B, 10C, 10D, 11A, 11B and 11C)

An oxygen-permeable membrane 28 was coated onto the necessary portions according to the following steps [18] to [20].

Figure 9A:
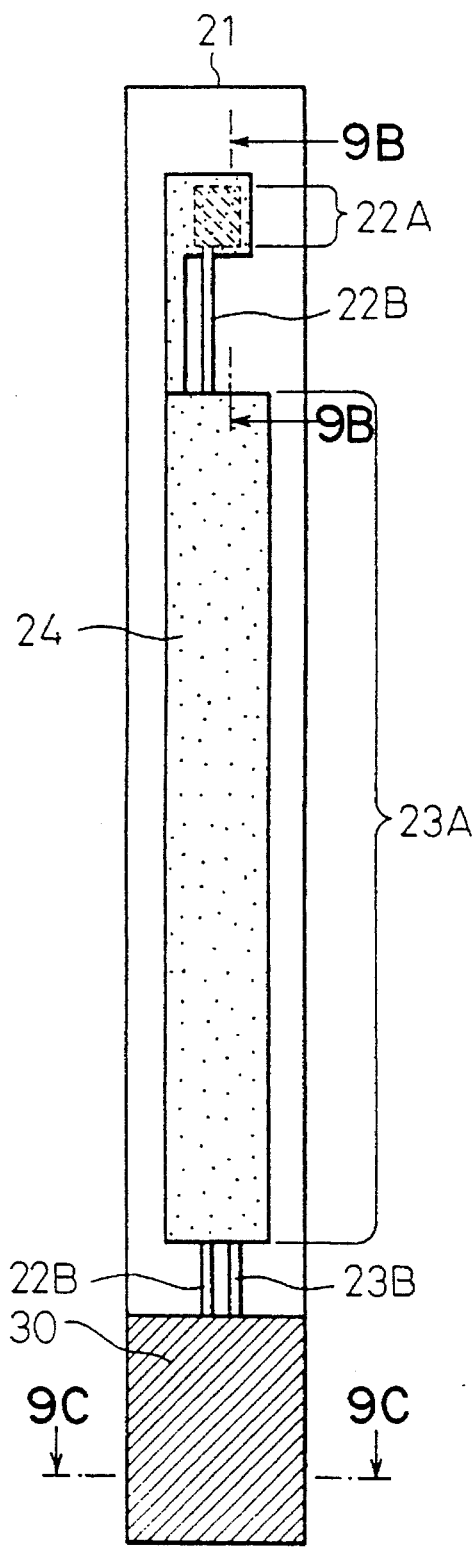
Figure 9B:
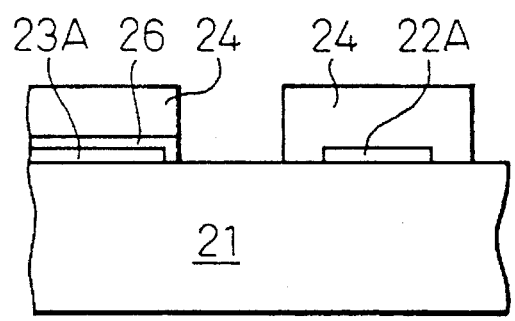
Figure 9C:
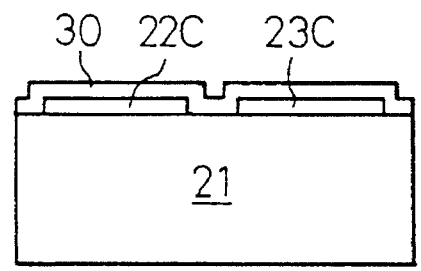
Figure 10A:
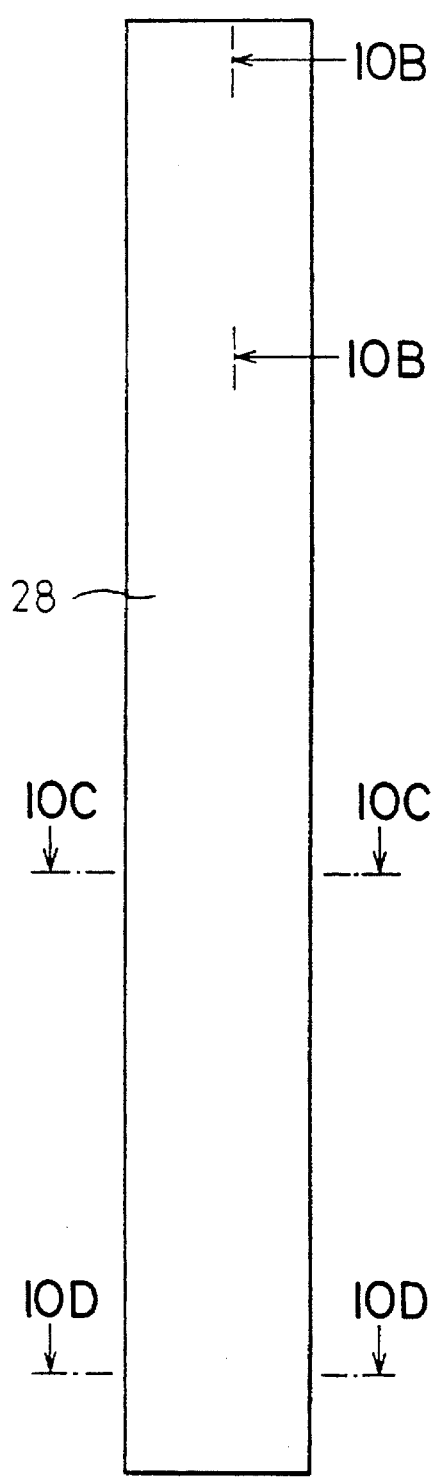
Figure 10B:
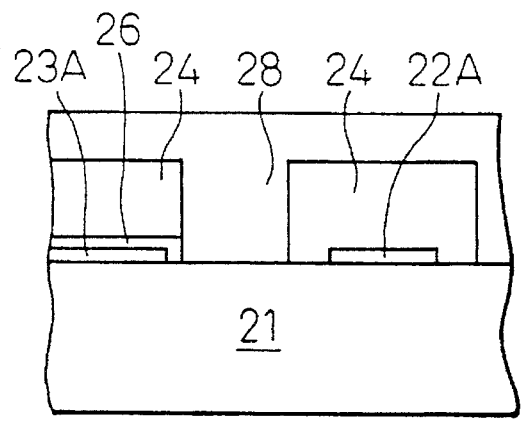
Figure 10C:
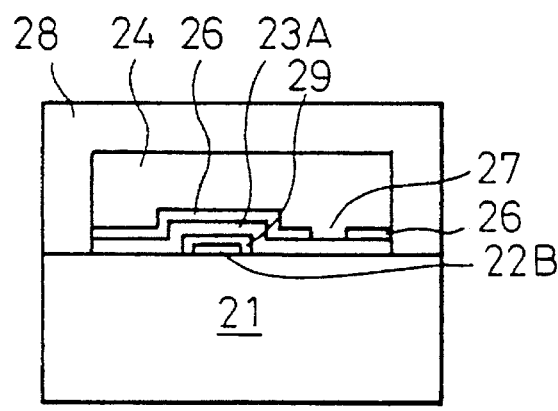
Figure 10D:
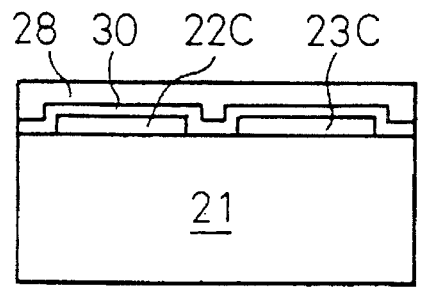

[18] A thermosetting peelable coating (XB-801, manufactured by Fujikura Kasei Corp.) was screen-printed in a thickness of 100 μm on the pad region (substrate region including the pads 22C, 23C), and the resultant print was heated at 80° C. for 20 min, thereby curing the print. Thus, a releasable mask 30 was formed (FIGS. 9A, 9B and 9C).

[19] Then, a silicone resin 28 (SE9176, manufactured by Dow Corning Toray Silicone Company, Ltd.) for constituting a oxygen-permeable membrane was spin-coated, and the resultant coating was heated in a moistened thermostatic chamber at 80° C. for 60 min, thereby curing the coating. The moistening was carried out by placing a water-containing Petri dish or beaker in the thermostatic chamber (FIGS. 10A, 10B, 10C and 10D).

Figure 11A:
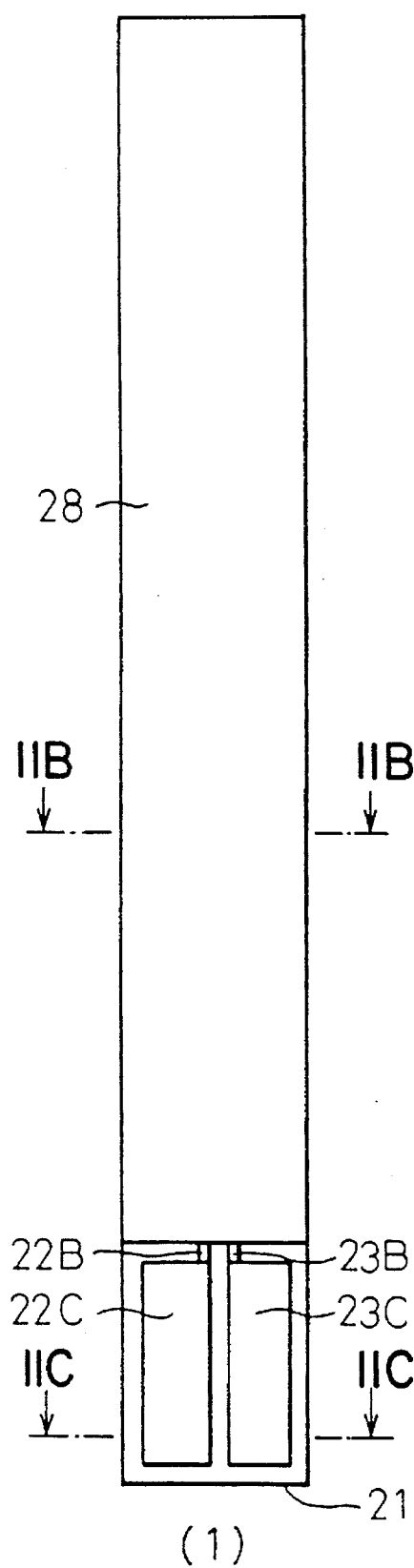
Figure 11B:
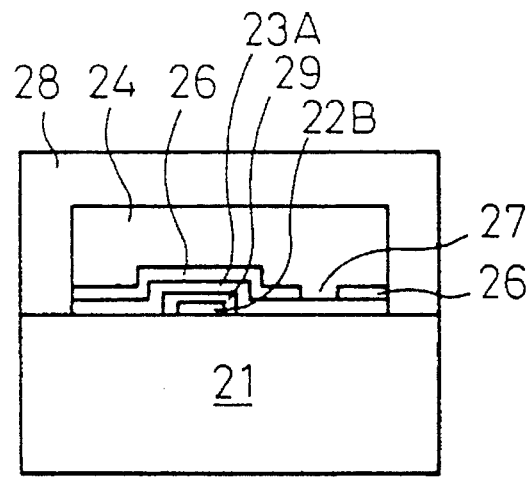
Figure 11C:
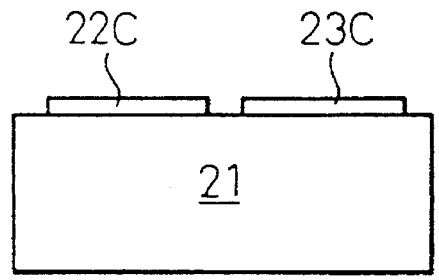

[20] The above mask 30 formed on the pad regions was peeled off with a pincette, thereby removing the pad regions together with the silicone resin 28 in its portion formed on the mask 30 to expose the pad regions (pad 22C, 23C) (FIGS. 11A, 11B and 11C). Thus, a miniaturized oxygen electrode of the present invention was prepared wherein the whole thereof except for the pad regions was covered with a oxygen-permeable membrane 28. In this example, the pads 22C and 23C were arranged in the widthwise direction of the substrate because the lead wire for external connection could be led out more easily than an embodiment where they were arranged in the longitudinal direction of the substrate.

Thus, a number of miniaturized oxygen electrodes 2 collectively formed on the glass substrate 21 were cut into miniaturized oxygen electrode chips.

For the miniaturized oxygen electrode, shown in FIGS. 2A, 2B and 2C, according to the present invention, the response can be enhanced by forming the oxygen-permeable membrane 28, on the oxygen-sensitive section 22S (FIG. 2A) within the active section 22A of the cathode pattern 22, in a smaller thickness than the other regions. Such a miniaturized oxygen electrode can be prepared by the following procedures.

The step 1 through [19] of the step 5 are repeated.

Figure 12A:
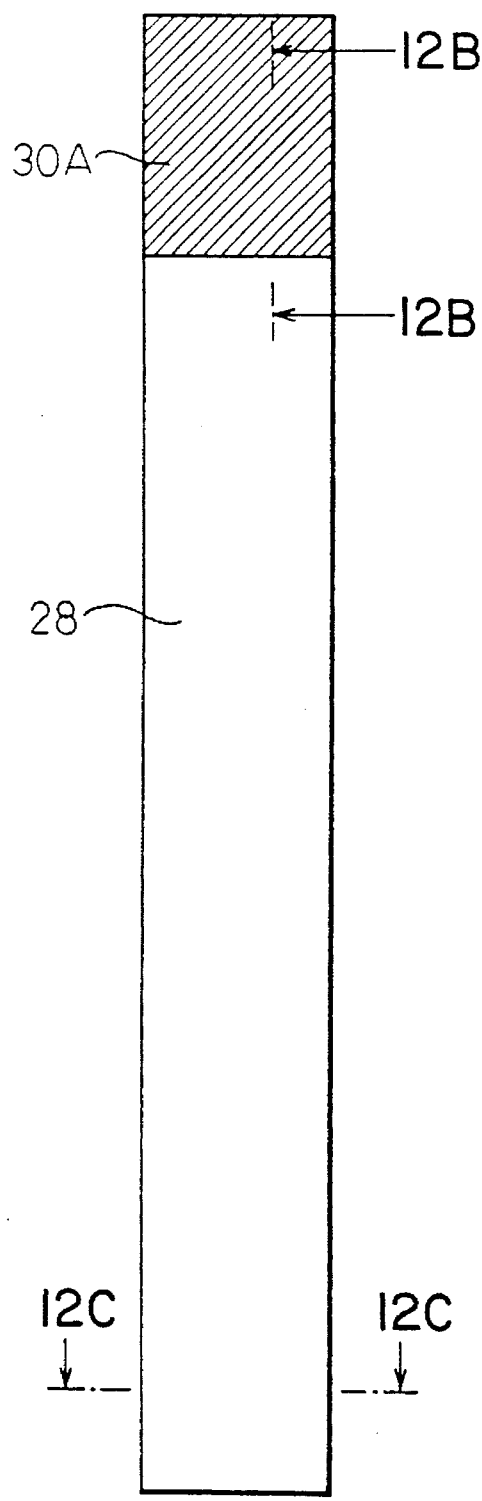
Figure 12B:
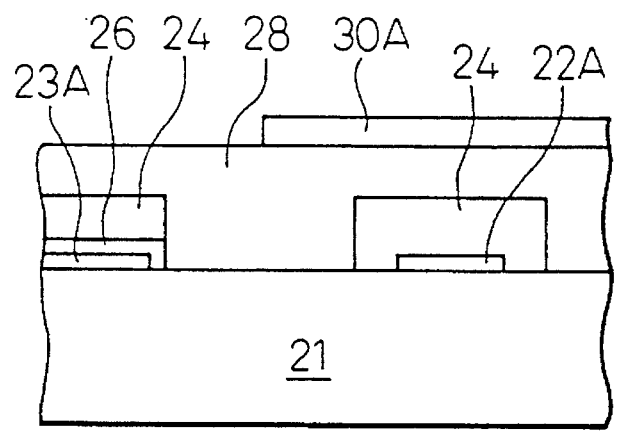
Figure 12C:
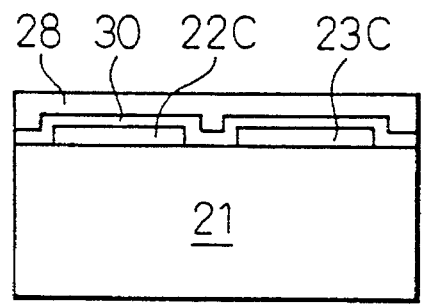

Then, a second peelable mask 30A is formed on the silicone rubber membrane 28 (FIGS. 12A and 12B) present on the oxygen-sensitive section 22S (FIG. 2A) within the active section 22A of the cathode pattern 22 in the same manner as in the above step [18].

Figure 13A:
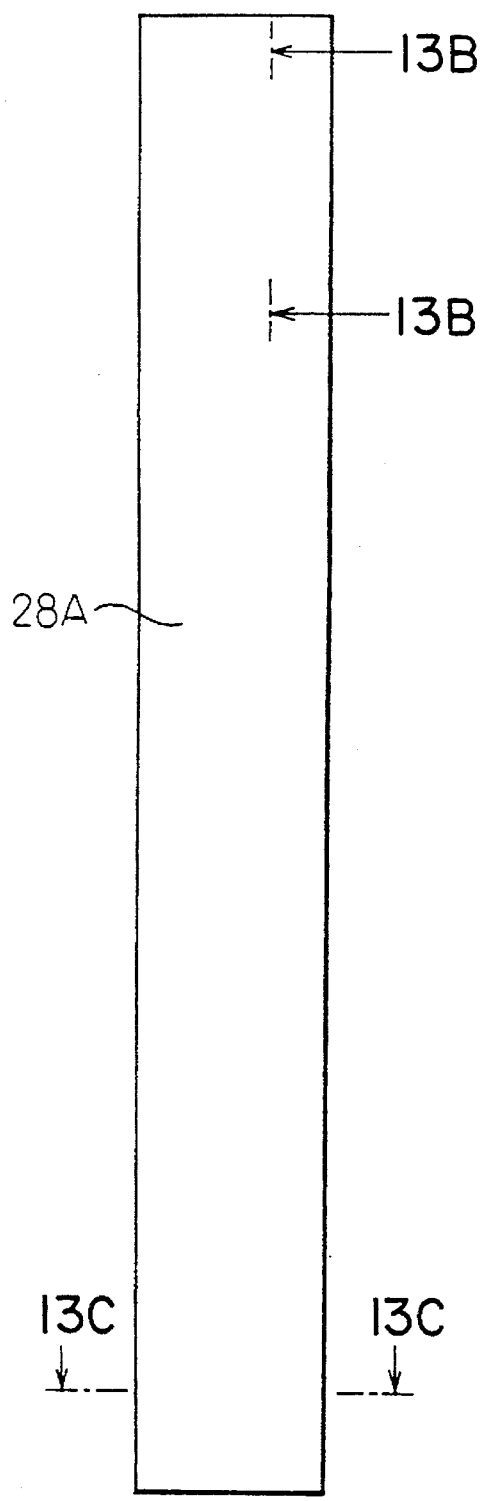
Figure 13B:
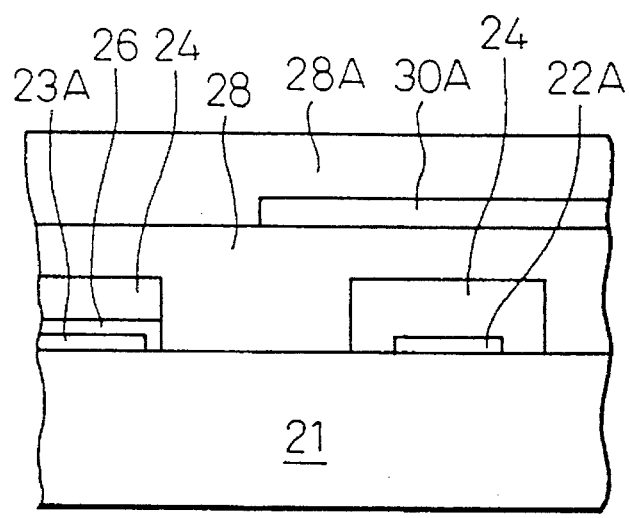
Figure 13C:
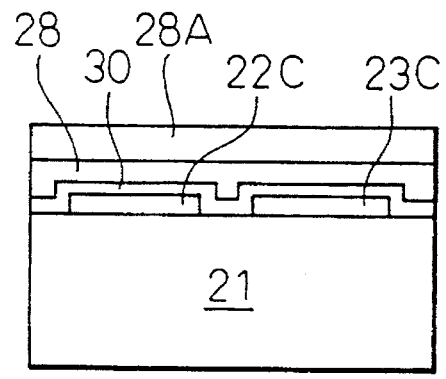

Then, a second silicone rubber membrane 28A is formed on the whole surface of the substrate including the second peelable mask 30A and the silicone rubber membrane (first silicone resin membrane) 28 in its exposed area (FIGS. 13A, 13B and 13C) in the same manner as in the above [19].

Finally, the peelable mask 30 in the pad regions is peeled off in the same manner as in the above [20], thereby removing the mask 30 together with the silicone rubber layers 28 and 28A formed on the mask 30 to expose the pad regions (pad 22C, 23C). Further, the second peelable mask 30A is peeled off to remove the second silicone rubber layer 28A on the oxygen-sensitive section 22S while leaving the first silicone resin layer 28. Thus, in the silicone resin layer on the oxygen-sensitive section 22S, the first silicone resin layer 28 alone constitutes the thickness of the silicone resin layer. Therefore, the thickness of this region is smaller than the thickness of the silicone resin layer in the other regions (the total thickness of the first silicone resin layer 28 and the second silicone resin layer 28A) (FIGS. 14A, 14B and 14C).

In general, when potassium chloride or the like is used as the electrolyte, the anode is constituted in the form of an electrode of silver and an insoluble halide thereof, such as silver/silver chloride or silver/silver bromide. In order for the silver anode to react with the electrolyte to constitute such an electrode, the electrolyte should contain a halogen ion. For this purpose, the electrolyte should contain a halogen ion source. Preferably, it contains a buffer for maintaining the pH value of the electrolyte constant.

The major part of the anode 23A is covered with the electrolyte-impermeable membrane 26, such as a polyimide, so that the anode 23A comes into contact with the electrolyte-containing material 24 only in the opening 27 of the layer 26. The reason for this is as follows. Specifically, the larger the anode area, the longer the life of the miniaturized oxygen electrode. However, a stabilizing time taken for the outermost surface of the anode to gradually change from Ag in the initial form to AgCl increases with an increase in the anode area. When the major portion of the anode is covered with an electrolyte-impermeable membrane to allow the anode to come into contact with the electrolyte-containing material only in the opening, it becomes possible to attain a combination of prolonged service life with a shortening of the time for substantial stabilization.

Although in Example 1 an embodiment was described where the lead wire 22B for the cathode 22A was disposed below the anode 23A, it is in some cases advantageous that, as shown in FIG. 15A, in a miniaturized oxygen electrode 41, a lead wire 43B of an anode 43A is disposed below a cathode 42A.

Further, although in Example 1 a miniaturized oxygen electrode having a bipolar construction of the cathode 22A and the anode 23A has been described, the present invention can be applied, if necessary, to miniaturized oxygen electrodes having a tripolar construction. For example, as shown in FIG. 15B or 15C, in the case of a miniaturized oxygen electrode 51 having a tripolar construction of a working electrode 52A, a reference electrode 53A, and a counter electrode 54A, it is advantageous in that a lead wire 52B for the working electrode 52A (FIG. 15B) or lead wires 52B, 53B for the working electrode 52A and the reference electrode 53A (FIG. 15C) are disposed below the counter electrode 54A occupying a relatively large area.

The lead wires (43B, 52B, 53B) disposed in the lower position are each covered with an insulating layer and insulated from each electrode pattern provided on the upper position, although this is not shown in FIGS. 15A, 15B and 15C.

Example 2

According to one of the desired embodiments of the present invention, as shown in FIG. 2C, in a miniaturized oxygen electrode 3, a lead wire portion 22B for a cathode pattern 22 and an insulating layer 29 provided thereon are housed in a laminate form within a groove 32 provided in a substrate 31, thereby filling the groove 32 for leveling, and an active section 23A of an anode pattern 23 is provided thereon.

The formation of other patterns on the flattened portion eliminates the problem of step coverage.

The structure having a groove 32 shown in FIG. 2C was prepared according to the following steps.

Step 01: Preparation of substrate

In this embodiment, a silicon substrate on which a groove can be easily formed by a semiconductor production process is more suitable than the glass substrate used in Example 1.

[1] A 400 μm-thick silicon substrate having a (100) face was prepared and cleaned with a solution mixture of hydrogen peroxide and ammonia, and with concentrated nitric acid.

[2] The cleaned silicon substrate is subjected to wet thermal oxidation at 1000° C. for 200 min to form a 1.0 μm-thick $SiO_2$ insulating layer on both surfaces of the substrate.

Step 02: Removal of $SiO_2$ oxide layer in portion where groove is to be formed

[3] A negative-working photoresist (OMR-83, manufactured by Tokyo Ohka Kogyo Co., Ltd.) was coated on one surface of the silicon substrate with an oxide layer formed thereon, and the resultant coating was baked at 80° C. for 30 min. Then, the photoresist was exposed, developed, and rinsed, thereby removing the photoresist in a portion where a cathode lead wire 22B is to be formed.

[4] The same negative-working photoresist was coated on the whole surface of the substrate remote from the surface which was subjected to the treatment in the above [3], and the resultant coating was baked at 150° C. for 30 min.

[5] The substrate was immersed in a solution mixture of 1 part by volume of 50% hydrofluoric acid and 6 parts by volume of 40% ammonium fluoride to remove the $SiO_2$ oxide layer exposed in the above [3], thereby exposing the surface of the silicon substrate in a portion where a cathode lead wire 22B is to be formed.

[6] The substrate was immersed in a solution mixture of 2 parts by volume of sulfuric acid and 1 part by volume of hydrogen peroxide to peel off the negative-working photoresist.

Step 03: Formation of groove

[7] The substrate was immersed in a 35% potassium hydroxide solution at 80° C. for one hr to anisotropically etch the silicon substrate in the portion exposed in the above [5], thereby forming the above groove 32 in a portion where a cathode lead wire 22B is to be formed.

[8] The substrate was cleaned with a solution mixture of hydrogen peroxide and ammonia and with concentrated nitric acid.

[9] The substrate was subjected to wet oxidation at 1000° C. for 200 min to form a 1.0 μm-thick SiO$_2$ insulating layer (which is the same as that indicated by reference numeral 31A in FIGS. 16C and 16C) on both surfaces of the substrate.

After the formation of the groove 32 (FIG. 2C), a miniaturized oxygen electrode was prepared by repeating the procedure after [2] of Example 1.

Example 3

According to another preferred embodiment of the present invention, in the structure shown in FIGS. 2A, 2B and 2C, a recess is provided on the anode 23A in its portion below which no cathode lead wire 22B is extended, thereby increasing the amount of the electrolyte-containing material 24 held on the anode 23A through an electrolyte-impermeable membrane. In this case, the same silicon substrate as in Example 2 is used, and a groove is formed in the same manner as in Example 2.

As indicated by oblique lines in FIG. 16A, in a portion 33 below which no cathode lead wire 22B is extended, the anode 23A is formed along the inner wall of the recess (or groove) 33 provided within the silicon substrate 31, so that a recess (or a groove) 34 corresponding to the anode 23A per se is formed (FIG. 16B).

According to a further preferred embodiment, in the structure of FIG. 2, the lower portion of a liquid junction (a portion consisting of an electrolyte-containing material alone) 24X where the electrolyte-containing material 24 connects a cathode 22A to an anode 23A can be housed within a groove 35 provided on a silicon substrate 31, as shown in FIGS. 16C and 16D. When the width of the liquid junction 24X is narrow or the composition of the electrolyte-containing material 24 has a high concentration with the thickness of the liquid junction 24X being small, the conductance of the liquid junction 24X is lowered, which is likely to affect the stability of the miniaturized oxygen electrode. The provision of the groove 35 ensures the conductance of the liquid junction 24X.

The recess (groove) 33 or 35 in the silicon substrate 31 can be formed according to the same procedure as in the groove 32 described in Example 2. The layer indicated by reference numeral 31A in FIGS. 16B and 16D is an SiO$_2$ insulating layer formed by forming a groove 33 or 35 on a silicon substrate 31 and conducting wet oxidation in the same manner as in the above step 03, procedure [9] of Example 2.

The miniaturized oxygen electrodes prepared in Examples 1 to 3 can be immersed in water at room temperature overnight or for a longer period of time or alternatively treated in an autoclave at 120° C. and a pressure difference of 1.2 arm for 15 min to feed water in a water vapor form into the electrolyte, whereby the electrodes can function as an oxygen electrode.

Example 4

Figure 17:
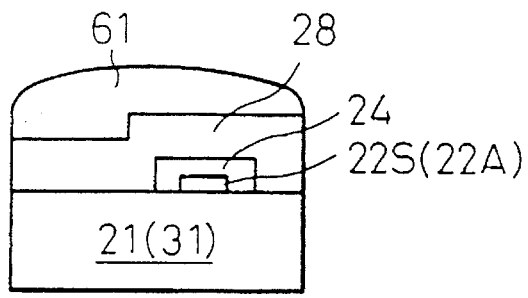
FIG. 17 shows a cross-sectional view of a miniaturized biosensor of the present invention.

A miniaturized biosensor as shown in FIG. 17 was prepared. This biosensor is such that a glucose-immobilized membrane 61 with an enzyme (glucose oxidase) being immobilized thereto is provided on the sensitive section 22S (22A) of a miniaturized oxygen electrode prepared in any one of Examples 1 to 3. This was done by immersing the sensitive section 22S (22A) of a miniaturized oxygen electrode in a solution of 1 mg of glucose oxidase in 20 ml of a solution containing 5% by weight of bovine serum albumin and 5% by weight of glutaraldehyde and then drying the sensitive section 22S (22A).

Example 5

Figure 18:
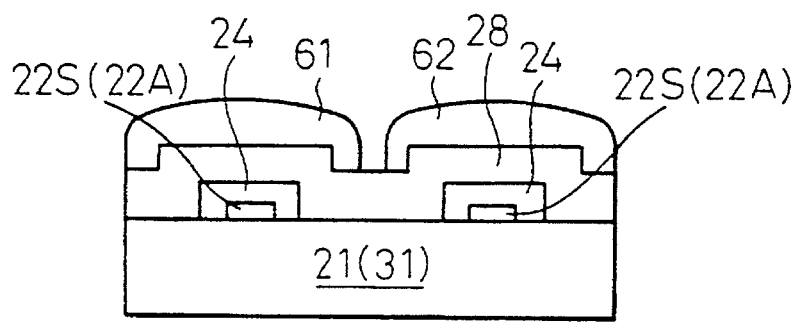
FIG. 18 shows a cross-sectional view of an integrated biosensor of the present invention.

An integrated biosensor shown in FIG. 18 was prepared. This biosensor was prepared by arranging two miniaturized oxygen electrodes parallel to each other in a chip in the same manner as in Examples 1 to 3 and repeating the procedure of Example 4 to provide a glucose oxidase-immobilized membrane 61 on one of the miniaturized oxygen electrodes in its sensitive portion with a glutamic acid oxidase-immobilized membrane 62 being provided on the other miniaturized oxygen electrode in its sensitive portion.

Figure 19:
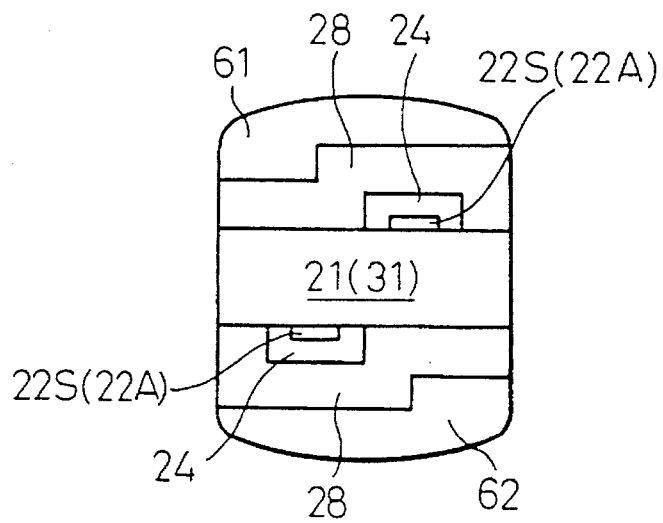
FIG. 19 shows a cross-sectional view of an integrated biosensor according to another embodiment of the present invention.

An integrated biosensor, as shown in FIG. 19, comprising a miniaturized oxygen electrode formed on both surfaces of the substrate can be prepared in the same manner as in Examples 1 to 3.

Figure 20:
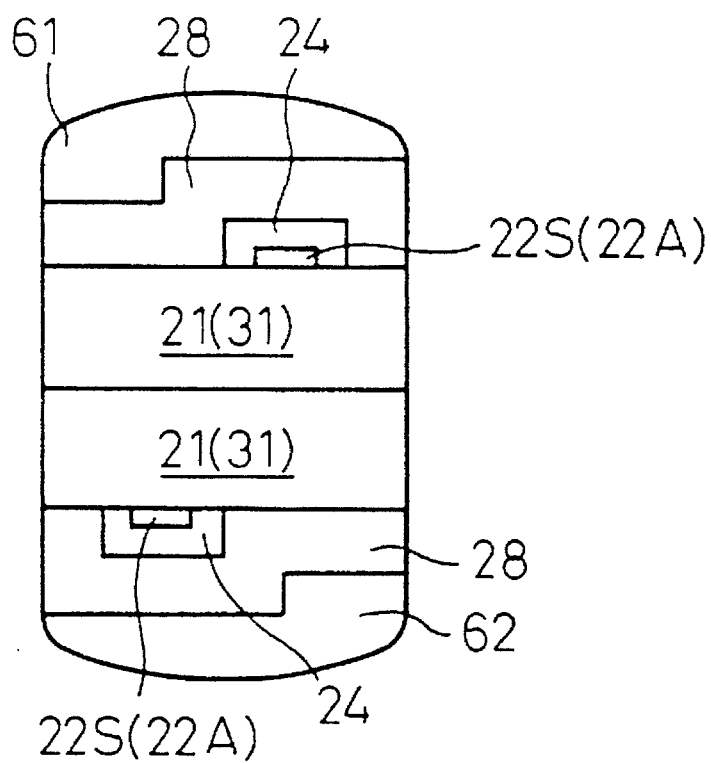
FIG. 20 shows a cross-sectional view of an integrated biosensor according to a further embodiment of the present invention.

Further, an integrated biosensor, as shown in FIG. 20, can be prepared which comprises miniaturized oxygen electrodes, prepared in Examples 1 to 3, bonded to each other so that the back surfaces of the substrates face each other.

For the biosensor prepared in Example 4 or 5, since an enzyme is immobilized thereon, no autoclave treatment can be carried out for activation. Instead, activation is carried out by immersing a chip with an enzyme being immobilized thereon in water at room temperature for not less than 12 hours to feed water into the electrolyte-containing material.

Figure 21:
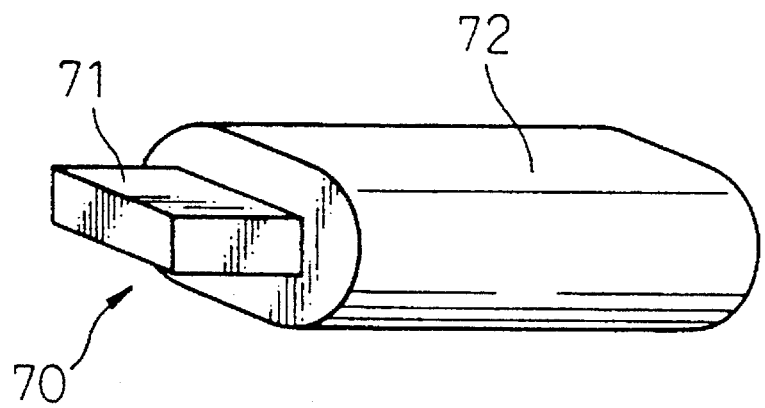
FIG. 21 shows a perspective view of a miniaturized oxygen electrode or a biosensor, according to the present invention, with all the portions except for a sensitive portion and its vicinity being housed within a tube.

For the miniaturized oxygen electrodes and biosensors prepared in Examples 1 to 5, only a portion in the vicinity of the cathode serves as the sensitive section. Therefore, as shown in FIG. 21, the portions other than the periphery 71 of the sensitive section of the miniaturized oxygen electrode 70 is preferably housed in a tube 72 such as a silicone tube, from the viewpoint of preventing evaporation of water.

As described above, the miniaturized oxygen electrode of the present invention has such a three-dimensional arrangement that the lead wire portion of at least one electrode pattern is extended below the active section of the other at least one electrode pattern, with an insulating layer intervening between the lead wire portion and the active section, enabling a larger number of patterns to coexist within the same area of the substrate as compared with the conventional miniaturized oxygen electrode. This in turn enables the width of the miniaturized oxygen electrode to be made smaller than that of the conventional miniaturized oxygen electrode having a planar arrangement. In this case, the insulation of the three-dimensionally laminated patterns from each other can be ensured by an insulating layer interposed therebetween, and even though peeling occurs in the oxygen-permeable membrane, there is no possibility that the electrolyte reaches the lead wire portion.

We claim:

1. A miniaturized oxygen electrode comprising:

an insulating substrate;

a first electrode pattern on the substrate and having a first active section, a first terminal section for external connection, and a first lead wire portion electrically interconnecting the first active section and the first terminal section;

a second electrode pattern on the substrate and having a second active section, a second terminal section for external connection, and a second lead wire portion electrically interconnecting the second active section and the second terminal section;

a layer of an electrolyte-containing material which contacts and electrically interconnects said first and second active sections;

an oxygen-permeable membrane covering said electrolyte-containing material;

said first lead wire portion being elongated and being disposed to extend beneath said second active section; and an insulating layer disposed between the first lead wire portion and the second active section.

2. A miniaturized oxygen electrode as set forth in claim 1, wherein a groove is provided in said substrate, and said first lead wire portion and said insulating layer are arranged within the groove, said second active section being located over said groove in covering relationship thereto.

3. A miniaturized oxygen electrode as set forth in claim 1, wherein one of said electrode patterns comprises an anode and another of said electrode patterns comprises a cathode.

4. A miniaturized oxygen electrode as set forth in claim 3, wherein a groove is provided in said substrate, and said first lead wire portion and said insulating layer are arranged within the groove, said second active section being located over said groove in covering relationship thereto.

5. A miniaturized oxygen electrode as set forth in claim 3, wherein said first and second active sections include a silver outer layer and said electrolyte-containing material contains a halogen ion source.

6. A miniaturized oxygen electrode as set forth in claim 3, wherein the active section of the anode is covered with an electrolyte-impermeable membrane having good adhesion, wherein a small opening is provided in the membrane, and wherein the active section of the anode is in contact with said electrolyte-containing material through said opening.

7. A miniaturized oxygen electrode as set forth in claim 6, wherein said electrolyte-impermeable membrane is formed of a polyimide.

8. A miniaturized oxygen electrode as set forth in claim 1, wherein is included three electrode patterns corresponding respectively to a working electrode, a reference electrode, and a counter electrode.

9. A miniaturized oxygen electrode as set forth in claim 8, wherein each of said patterns includes an active section, wherein the active sections of the working electrode and the reference electrode each include an outer silver layer, wherein the silver layer of the reference electrode comprises an outer coating of silver chloride, wherein the active section of the counter electrode includes an outer gold layer, and wherein said electrolyte-containing material contains a halogen ion source.

10. A miniaturized oxygen electrode as set forth in claim 1, wherein said insulating substrate is formed of silicon or glass.

11. A miniaturized oxygen electrode as set forth in claim 1, wherein said insulating substrate is formed of a polyimide.

12. A miniaturized oxygen electrode as set forth in claim 1, wherein a recess is provided in said second active section at a position which is not over said first lead wire portion.

13. A miniaturized oxygen electrode as set forth in claim 1, wherein a groove is provided in said substrate, and said layer of an electrolyte-containing material includes a liquid junction interconnecting said first and second active sections, said liquid junction being housed in said groove.

14. A miniaturized oxygen electrode as set forth in claim 1, wherein a water-impermeable membrane having good adhesion is provided on the substrate, and wherein said electrolyte-containing material and said oxygen-permeable membrane are formed on said water-impermeable membrane.

15. A miniaturized oxygen electrode as set forth in claim 14, wherein said water-impermeable membrane is formed of a polyimide.

16. A miniaturized oxygen electrode as set forth in claim 1, wherein said electrolyte-containing material is initially water-free and is activatable by water necessary for a reduction reaction of oxygen which accompanies said oxygen in the form of water vapor as the oxygen passes through said oxygen-permeable membrane and into the electrolyte-containing material.

17. A miniaturized oxygen electrode as set forth in claim 16, wherein said electrolyte-containing material comprises a dispersion of a powdered electrolyte component and a buffer component in a polyvinyl pyrrolidone carrier.

18. A miniaturized oxygen electrode as set forth in claim 1, wherein said oxygen-permeable membrane is formed of silicone rubber.

19. A miniaturized oxygen electrode as set forth in claim 1, wherein one of said active sections includes an oxygen-sensitive area, and the oxygen-permeable membrane has a first region which covers a portion of the electrolyte-containing material that contacts said area, said first region of the oxygen-permeable membrane having a thickness which is less than the thickness of other regions of the membrane whereby the response of the electrode is enhanced.

20. A miniaturized oxygen electrode as set forth in claim 1, wherein said substrate is elongated and said electrode patterns are elongated and arranged to extend along the substrate with said terminal sections disposed at one end of said substrate.

21. A miniaturized oxygen electrode as set forth in claim 1, wherein is included a removable vessel for housing the electrode to prevent evaporation of water.

22. A miniaturized biosensor including a miniaturized oxygen electrode comprising:

an insulating substrate;

a first electrode pattern on the substrate and having a first active section, a first terminal section for external connection, and a first lead wire portion electrically interconnecting the first active section and the first terminal section;

a second electrode pattern on the substrate and having a second active section, a second terminal section for external connection, and a second lead wire portion electrically interconnecting the second active section and the second terminal section;

a layer of an electrolyte-containing material which contacts and electrically interconnects said first and second active sections;

an oxygen-permeable membrane covering said electrolyte-containing material;

said first lead wire portion being elongated and being disposed to extend beneath said second active section;

an insulating layer disposed between the first lead wire portion and the second active section; and an organism-related substance including an enzyme or a microorganism immobilized on one of said active sections to present an oxygen-sensitive area.

23. An integrated biosensor comprising a plurality of miniaturized biosensors as set forth in claim 22, wherein different organism-related substances are supported respectively on the oxygen-sensitive areas of the miniaturized biosensors, said miniaturized biosensors being provided on an integrated substrate made up of the respective substrates of the miniaturized biosensors.

24. An integrated biosensor as set forth in claim 23, wherein said miniaturized biosensors are arranged on a single planar surface of said integrated substrate.

25. An integrated biosensor as set forth in claim 23, wherein said miniaturized biosensors are arranged on respective different surfaces of said integrated substrate.

26. An integrated biosensor as set forth in claim 25, wherein the respective substrates of at least two of said miniaturized biosensors are bonded together in said integrated substrate with the miniaturized biosensors facing away from one another.

27. An integrated biosensor as set forth in claim 23, wherein is included a removable vessel for housing the respective electrodes to prevent evaporation of water.

28. A miniaturized biosensor as set forth in claim 22, wherein is included a removable vessel for housing the electrode to prevent evaporation of water.

29. A process for producing a miniaturized oxygen electrode comprising:

forming an electrode structure including an insulating substrate, an electrode pattern having a terminal section and an active section, an insulating layer pattern, and an electrolyte-containing material pattern, said patterns being disposed on said substrate;

forming a first peelable resin pattern over said terminal section;

forming a first oxygen-permeable membrane over the entire structure including over the substrate and said patterns;

forming a second peelable resin pattern on said first oxygen-permeable membrane, said second peelable resin pattern being positioned over an oxygen-sensitive area of the active section of said electrode pattern;

forming a second oxygen-permeable membrane over the entire structure including over the second peelable resin pattern and over an area of the first oxygen-permeable membrane that is not covered by the second peelable resin pattern;

peeling said first peelable resin pattern to expose the terminal portion of said electrode pattern; and peeling said second peelable resin pattern to remove a portion of said second oxygen-permeable membrane located over said oxygen-sensitive area while leaving said first oxygen-permeable membrane located over said oxygen-sensitive area intact, whereby the total thickness of oxygen-permeable membrane located over said oxygen-sensitive area is less than the thickness of oxygen-permeable membrane located over other areas of the structure, to the end that the response of the electrode is enhanced.

* * * * *

UNITED STATES PATENT AND TRADEMARK OFFICE
CERTIFICATE OF CORRECTION

PATENT NO.   : 5,573,649
DATED        : November 12, 1996
INVENTOR(S)  : Sugama et al.

It is certified that error appears in the above-indentified patent and that said Letters Patent is hereby corrected as shown below:

Column 2, line 1, delete "collectivelymass-produced" and substitute --collectively mass-produced--;
    line 6, after "A1", insert --.--.

Column 11, line 4, delete "16C)" and substitute --16D)--;
    line 53, delete "arm" and substitute --atm--.

Signed and Sealed this

Twenty-fifth Day of March, 1997

Attest:

BRUCE LEHMAN

*Attesting Officer*   Commissioner of Patents and Trademarks